(12) United States Patent
Kalafut et al.

(10) Patent No.: US 8,428,694 B2
(45) Date of Patent: Apr. 23, 2013

(54) METHODS FOR DETERMINATION OF PARAMETERS FOR A PROCEDURE, FOR ESTIMATION OF CARDIOPULMONARY FUNCTION AND FOR FLUID DELIVERY

(75) Inventors: John F. Kalafut, Pittsburgh, PA (US); Corey Kemper, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 316 days.

(21) Appl. No.: 12/669,292

(22) PCT Filed: Jun. 24, 2008

(86) PCT No.: PCT/US2008/067982
§ 371 (c)(1),
(2), (4) Date: Jan. 15, 2010

(87) PCT Pub. No.: WO2009/012023
PCT Pub. Date: Jan. 22, 2009

(65) Prior Publication Data
US 2010/0204572 A1 Aug. 12, 2010

Related U.S. Application Data

(60) Provisional application No. 60/950,148, filed on Jul. 17, 2007.

(51) Int. Cl.
*A61B 5/00* (2006.01)
(52) U.S. Cl.
USPC ............ 600/431; 600/420; 600/481; 604/19; 604/28; 604/67; 604/131; 382/128; 382/131
(58) Field of Classification Search .................. 600/420, 600/431, 481; 604/19, 28, 67, 131; 382/128, 382/131
See application file for complete search history.

(56) References Cited

U.S. PATENT DOCUMENTS 3,701,345 A 10/1972 Heilman et al.
3,812,843 A 5/1974 Wootten et al.
(Continued)

FOREIGN PATENT DOCUMENTS

CA 2045070 A1 2/1992
EP 0619122 A1 10/1994
(Continued)

OTHER PUBLICATIONS

International Search Report and Written Opinion from counterpart PCT Application PCT/2008/67982 filed Jun. 24, 2008.

(Continued)

*Primary Examiner* — Ruth S Smith
(74) *Attorney, Agent, or Firm* — James R. Stevenson

(57) ABSTRACT

Methods of determining at least one parameter for an injection procedure to be performed in combination with an imaging procedure may include injecting a test bolus of a contrast enhancement fluid having a contrast enhancing agent, scanning regions of interest with an imaging system as the test bolus flows therethrough to obtain therefrom a contrast time enhancement curve for each region of interest, extracting at least one discrete data point from each of the contrast time enhancement curves such that each of the discrete data points constitutes a pair of measurements on the contrast time enhancement curve corresponding thereto, substituting into a model the discrete data points extracted from the contrast time enhancement curves to obtain an estimate of values of physiological variables, and using the estimate to determine via the model the at least one parameter for the injection procedure to be performed in combination with the imaging procedure.

39 Claims, 18 Drawing Sheets

U.S. PATENT DOCUMENTS

| | | |
|---|---|---|
| 3,888,239 A | 6/1975 | Rubinstein |
| 3,898,983 A | 8/1975 | Elam |
| 4,135,247 A | 1/1979 | Gordon et al. |
| 4,151,845 A | 5/1979 | Clemens |
| 4,207,871 A | 6/1980 | Jenkins |
| 4,280,494 A | 7/1981 | Cosgrove, Jr. et al. |
| 4,319,568 A | 3/1982 | Tregoning |
| 4,340,153 A | 7/1982 | Spivey |
| 4,392,849 A | 7/1983 | Petre et al. |
| 4,396,385 A | 8/1983 | Kelly et al. |
| 4,409,966 A | 10/1983 | Lambrecht et al. |
| 4,444,198 A | 4/1984 | Petre |
| 4,477,923 A | 10/1984 | Baumann et al. |
| 4,479,761 A | 10/1984 | Bilstad et al. |
| 4,544,949 A | 10/1985 | Kurihara |
| 4,551,133 A | 11/1985 | Zegers de Beyl et al. |
| 4,585,009 A | 4/1986 | Barker et al. |
| 4,611,340 A | 9/1986 | Okazaki |
| 4,633,307 A | 12/1986 | Honda |
| 4,634,426 A | 1/1987 | Kamen |
| 4,636,144 A | 1/1987 | Abe et al. |
| 4,710,166 A | 12/1987 | Thompson et al. |
| 4,723,261 A | 2/1988 | Janssen et al. |
| 4,798,590 A | 1/1989 | O'Leary et al. |
| 4,838,856 A | 6/1989 | Mulreany et al. |
| 4,853,521 A | 8/1989 | Claeys et al. |
| 4,854,324 A | 8/1989 | Hirschman et al. |
| 4,874,359 A | 10/1989 | White et al. |
| 4,880,014 A | 11/1989 | Zarowitz et al. |
| 4,903,705 A | 2/1990 | Imamura et al. |
| 4,913,154 A | 4/1990 | Ermert et al. |
| 4,925,444 A | 5/1990 | Orkin et al. |
| 4,943,279 A | 7/1990 | Samiotes et al. |
| 4,966,579 A | 10/1990 | Polaschegg |
| 5,018,173 A | 5/1991 | Komai et al. |
| 5,034,987 A | 7/1991 | Fujimoto et al. |
| 5,040,537 A | 8/1991 | Katakura |
| 5,078,683 A | 1/1992 | Sancoff et al. |
| 5,088,981 A | 2/1992 | Howson et al. |
| 5,104,374 A | 4/1992 | Bishko et al. |
| 5,111,492 A | 5/1992 | Klausz |
| 5,128,121 A | 7/1992 | Berg et al. |
| 5,135,000 A | 8/1992 | Akselrod et al. |
| 5,180,896 A | 1/1993 | Gibby et al. |
| 5,300,031 A | 4/1994 | Neer et al. |
| 5,301,672 A | 4/1994 | Kalender |
| 5,317,506 A | 5/1994 | Coutre et al. |
| 5,339,799 A | 8/1994 | Kami et al. |
| 5,349,625 A | 9/1994 | Born et al. |
| 5,361,761 A | 11/1994 | Van Lysel et al. |
| 5,368,562 A | 11/1994 | Blomquist et al. |
| 5,368,567 A | 11/1994 | Lee |
| 5,382,232 A | 1/1995 | Hague et al. |
| 5,383,858 A | 1/1995 | Reilly et al. |
| 5,385,540 A | 1/1995 | Abbott et al. |
| 5,417,213 A | 5/1995 | Prince |
| 5,445,621 A | 8/1995 | Poli et al. |
| 5,456,255 A | 10/1995 | Abe et al. |
| 5,458,128 A | 10/1995 | Polanyi et al. |
| 5,459,769 A | 10/1995 | Brown |
| 5,469,849 A | 11/1995 | Sasaki et al. |
| 5,472,403 A | 12/1995 | Cornacchia et al. |
| 5,485,831 A | 1/1996 | Holdsworth et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,522,798 A | 6/1996 | Johnson et al. |
| 5,531,679 A | 7/1996 | Schulman et al. |
| 5,569,181 A | 10/1996 | Heilman et al. |
| 5,573,515 A | 11/1996 | Wilson et al. |
| 5,583,902 A | 12/1996 | Bae |
| 5,687,208 A | 11/1997 | Bae et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,840,026 A | 11/1998 | Uber, III et al. |
| 5,843,037 A | 12/1998 | Uber, III |
| 5,865,744 A | 2/1999 | Lemelson |
| 5,881,124 A | 3/1999 | Giger et al. |
| 6,055,985 A | 5/2000 | Bae et al. |
| 6,073,042 A | 6/2000 | Simonetti |
| 6,201,889 B1 | 3/2001 | Vannah |
| 6,236,706 B1 | 5/2001 | Hsieh |
| 6,317,623 B1 | 11/2001 | Griffiths et al. |
| 6,344,030 B1 | 2/2002 | Duchon et al. |
| 6,385,483 B1 | 5/2002 | Uber, III et al. |
| 6,397,097 B1 | 5/2002 | Requardt |
| 6,397,098 B1 | 5/2002 | Uber, III et al. |
| 6,402,697 B1 | 6/2002 | Calkins et al. |
| 6,470,889 B1 | 10/2002 | Bae et al. |
| 6,478,735 B1 | 11/2002 | Pope et al. |
| 6,556,695 B1 | 4/2003 | Packer et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,731,971 B2 | 5/2004 | Evans, III et al. |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,901,283 B2 | 5/2005 | Evans, III et al. |
| 6,970,735 B2 | 11/2005 | Uber, III et al. |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 2001/0056233 A1 | 12/2001 | Uber, III et al. |
| 2002/0026148 A1 | 2/2002 | Uber, III |
| 2004/0015078 A1 | 1/2004 | Evans, III et al. |
| 2004/0025452 A1 | 2/2004 | McLean |
| 2004/0064040 A1 | 4/2004 | Masuda et al. |
| 2004/0162484 A1 | 8/2004 | Nemoto |

FOREIGN PATENT DOCUMENTS

| | | |
|---|---|---|
| JP | 60253197 A | 12/1985 |
| JP | 62216199 A | 9/1987 |
| JP | 63290547 A | 11/1988 |
| JP | 1207038 A | 8/1989 |
| JP | 2224647 A | 9/1990 |
| JP | 2234747 A | 9/1990 |
| JP | 3055040 A | 3/1991 |
| JP | 4115677 A | 4/1992 |
| JP | 5084296 A | 4/1993 |
| JP | 7178169 A | 7/1995 |
| JP | 10211198 A | 8/1998 |
| JP | 2004298550 | 10/2004 |
| WO | 8500292 A1 | 1/1985 |
| WO | 8803815 A1 | 6/1988 |
| WO | 9415664 A1 | 7/1994 |
| WO | 9820919 A1 | 5/1998 |
| WO | 0061216 A1 | 10/2000 |
| WO | 2004012787 A2 | 2/2004 |

OTHER PUBLICATIONS

Sablayrolles, J-L, "Cardiac CT: Experience from Daily Practice", Advance CT, A GE Healthcare Publication. Aug. 2004.

"Digital Injector for Angiography", Sias. (Sep. 7, 1993).

"Angiomat 6000 Digital Injection System—Operator's Manual", Document No. 600950, Rev. Jan. 1990.

Fleischmann, Dominik, "Present and Future Trends in Multiple Detector-Row CT Applications; CT Angiography", Eur. Radiol. 12 (Suppl. 2) 2002.

Korosec, Frank, "Basic Principles of Phase-contrast, Time-of-flight, and Contrast-enhanced MR Angiography", 1999.

Baker, Aaron; et al. "Fluid Mechanics Analysis of a Spring-Loaded Jet Injector." IEEE Transactions on Biomedical Engineering, vol. 46, No. 2, Feb. 1999.

Cademartiri, F. and Luccichenti, G., et al. (2004) "Sixteen-Row Multislice Computed Tomography:Basic Concepts, Protocols, and Enhanced Clinical Application," Semin Ultrasound CT MR 25(1):2-16.

K.T. Bae, J.P. Heiken, and J.A. Brink, "Aortic and Hepatic Contrast Medium Enhancement at CT. Part I. Prediction and a Computer Model," Radiology, vol. 207, pp. 647-655, 1998.

K.T. Bae, "Peak Contrast Enhancement in CT and MR Angiography: When Does It Occur and Why? Pharmacokinetic Study in a Porcine Model," Radiology, vol. 227, pp. 809-816, 2003.

K.T. Bae et al., "Multiphasic Injection Method for Uniform Prolonged Vascular Enhancement at CT Angiography: Pharmacokinetic Analysis and Experimental Porcine Method," Radiology, vol. 216, pp. 872-880, 2000.

D. Fleischmann and K. Hittmair, "Mathematical Analysis of Arterial Enhancement and Optimization of Bolus Geometry for CT Angiography Using the Discrete Fourier Transform," J Comput Assist Tomogr, vol. 23, pp. 474-484, 1999.

Fisher and Teo, "Optimal Insulin Infusion Resulting from a Mathematical Model of Blood Glucose Dyanamics", IEEE Trans Biomed Eng, vol. 36(4), pp. 479-486, 1989.

Jacobs, "Algorithm for Optimal Linear Model-Based Control with Application to Pharmacokinetic Model-Driven Drug Delivery", IEEE Trans Biomed Eng, vol. 37(1), pp. 107-109, 1990.

Wada and Ward, "The Hybrid Model: A New Pharmacokinetic Model for Computer-Controlled Infusion Pumps", IEEE Trans. Biomed. Eng, vol. 41(2), pp. 134-142, 1994.

Wada and Ward, "Open Loop Control of Multiple Drug Effects in Anesthesia", IEEE Trans. Biomed Eng, vol. 42(7), pp. 666-677, 1995.

Neatpisarnvanit and Boston, "Estimation of Plasma Insulin from Plasma Glucose", IEEE Trans Biomed Eng, vol. 49 (11), pp. 1253-1259, 2002.

Gentilini et al., "A New Paradigm for the Closed-Loop Intraoperative Administration of Analgesics in Humans", IEEE Tran Biomed Eng, vol. 49(4), pp. 289-2999, 2002.

Mahnken, A.H., Henzler, D, et al., "Determination of Cardiac Output with Multislice Spiral Computed Tomography: A Validation Study", Invest Radiol 39(8): 451-4, 2004.

Mahnken, A.H., Klotz, E., et al., "Measurement of Cardiac Output from a Test-Bolus Injection in Multislice Computed Tomography", Eur Radiol 13(11): 2498-504, 2003.

Garrett, J.S., Lanzer, P., et al., "Measurement of Cardiac Output by Cine Computed Tomography", Am J Cardiol 56 (10): 657-61, 1985.

Fig. 2C

Test Bolus

| | Flow Rate | Volume | Duration |
|---|---|---|---|
| A | 5 | 20 | 00:04 |
| B | 5 | 40 | 00:08 |

| | ROI1 | ROI2 |
|---|---|---|
| Enter time to peak of test inj. [sec]: | 8.7 | 15.5 |
| Enter the peak of test inj. [HU]: | 236 | 175 |

Computer Protocol

Computed Parameters
Subject CO [L/min]: 5.67    Subject BV [L]: 0.475

Diagnostic Protocol
Suggested Scan Delay [sec]: 18

Please review values before entering into the injector

| | Flow Rate | Volume | Duration | Ratio |
|---|---|---|---|---|
| A | 3.5 | 55 | 00:16 | 40/60 |
| % | 3.5 | 26 | 00:08 | |
| B | 3.5 | 40 | 00:11 | |

210

Patient Parameters

| 64 | Subject Height [in] |
| 151 | Subject Weight [lbs] |
| 74 | Subject Age [yrs] |
| 74 | Avg. heart rate [bpm] |

○ Male  ● Female

Computed BMI: 25.9
Table CO [L/min]: 4.05

Max Flow Rate [ml/s]: 5 / 6 / 7
Contrast Concentration [mgI/ml]: 300 / 350 / 370
Catheter Gauge: 18 / 20 / 22

Injection Site ACF: ○ Left  ● Right

Scan Parameters

5.24  Scan Duration [sec]

Desired Peak Enh [HU]: 300 / 350
Target Enh [HU]: 250 / 300

[ Enter ]  [ Clear/New ]  [ Save ]

Fluid Volumes to Load
Contrast Load Vol [ml]: 175    Saline Load Vol [ml]: 150

Study Group Attenuation (n=70)

| Region Of Interest | Mean Attenuation (HU) | Standard Deviation | N{b} | 95% CI Lower | 95% CI Upper | p-value for $H_0: \mu=250HU$ |
|---|---|---|---|---|---|---|
| Asc. Aorta | 260.4 | 48.1 | 70 | 249.0 | 271.9 | 0.0736 |
| Left_Main | 272.6 | 52.9 | 67 | 259.7 | 285.5 | 0.0009 |
| LAD_Proximal | 270.4 | 49.3 | 64 | 258.1 | 282.7 | 0.0015 |
| LAD_Middle | 255.7 | 51.4 | 65 | 242.9 | 268.4 | 0.3769 |
| LAD_Distal | 236.8 | 55.7 | 50 | 221.0 | 252.7 | 0.101 |
| LCX_Proximal | 267.3 | 41.8 | 65 | 256.9 | 277.6 | 0.0015 |
| LCX_Middle | 255.0 | 45.9 | 64 | 243.6 | 266.5 | 0.384 |
| LCX_Distal | 241.4 | 36.4 | 48 | 230.8 | 252.0 | 0.1079 |
| RCA_Distal | 274.3 | 56.3 | 66 | 260.5 | 288.1 | 0.0008 |
| RCA_Middle | 268.0 | 56.2 | 65 | 254.1 | 281.9 | 0.012 |
| RCA_Proximal | 276.8 | 48.3 | 68 | 265.1 | 288.5 | ≤0.0001 |

Underlining = Mean>250 ; Double Underlining = p<0.05"

Fig. 10B

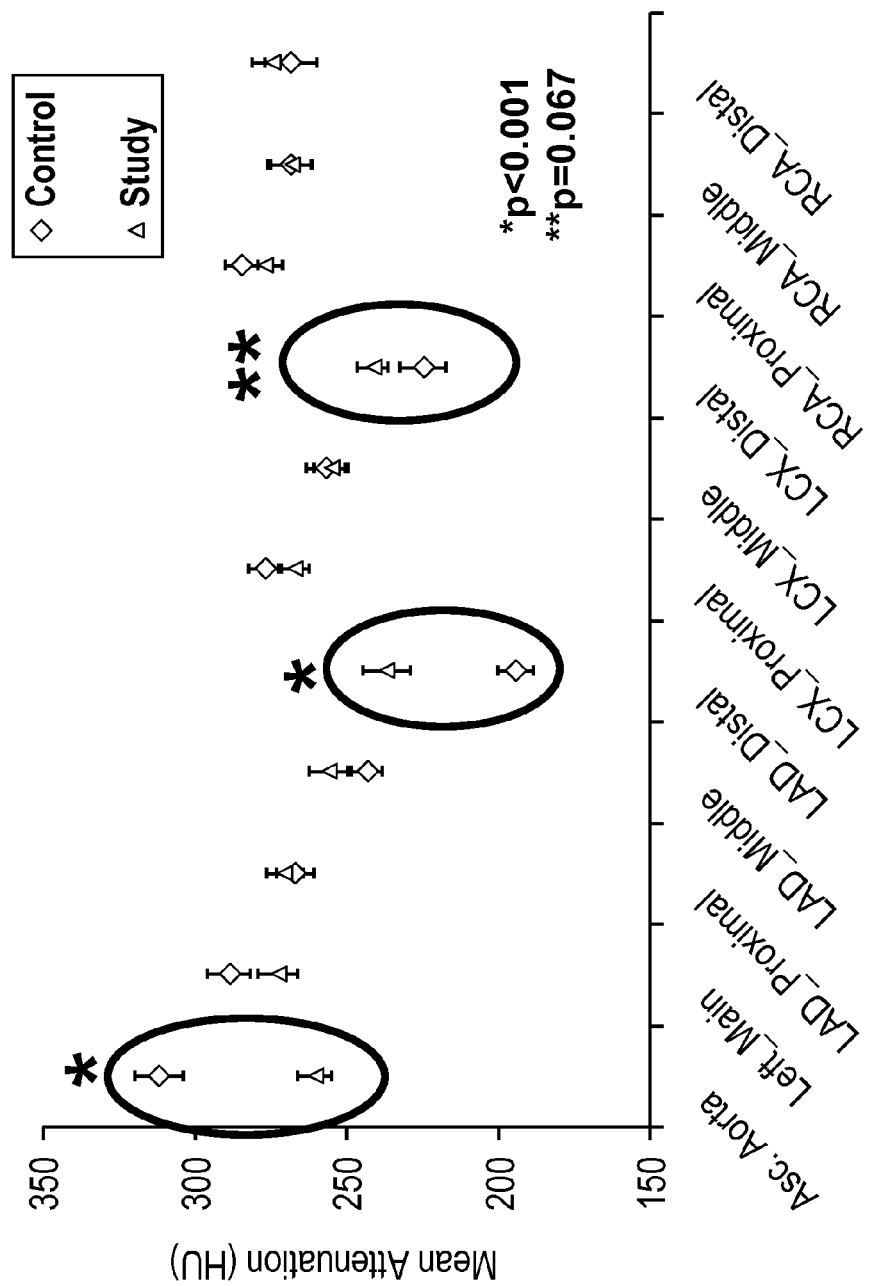

Fig. 16A

```
Protocol Generation Algorithm
1: Get Patient and Procedure information:
        a. Get contrast concentration:  C_i
        b. Get the maximum flow rate allowable: Q_MAX
        c. Get scan duration from user: ΔT
        d. Get Hounsfield to plasma concentration conversion
           factor HutoMgI for the scanner (default = 25
           HU/(mgI/ml) )
        e. Get desired LH enhancement at start and stop of scan
           window LHTarget and desired RH enhancement at start
           and stop of scan window RHTarget
        f. Generate a test bolus injection protocol, default Q
           is 5 ml/s and volume = 20 ml (4 second T_inj) at a
           50/50 contrast ratio, followed by saline flush
           phase, Q = 5 ml/s, vol = 40ml
2: From test bolus, get times to peak for the pulmonary artery
   enhancement curve and the ascending aorta enhancement curve
   from user: T_1 and T_2
3: Get peak enhancement values from the pulmonary artery and
   the ascending aorta bolus enhancement curves, and convert to
   concentration units using HutoMgI: C_1PA and C_2AO
4: ESTIMATE CARDIAC OUTPUT AND BLOOD VOLUME SUBROUTINE
        g. Compute Cardiac Output estimate (Q_CO) using Equation
           (7).
        h. Compute Blood Volume estimate (V_B) using Equation
           (6).
```

Fig. 16B

5: ESTIMATE DIAGNOSTIC PROTOCOL SUBROUTINE a. Compute $C_{LH\_peak}$, $C_{LH\_start}$, $C_{LH\_end}$, $C_{RH\_start}$, and $C_{RH\_end}$ enhancements using Equations 9, 10, 11, 12, and 13, respectively, for all admissible input values for $T_{start}$, $Q_{inj}$, $R_1$, $\Delta T_{inj1}$, $R_2$, $\Delta T_{inj2}$.

i. $T_{start}$ range = $T_{LH-arr}$ to 30 ii. $Q_{inj}$ range = $Q_{injTB}$ to min($Q_{injTB}$ + 1, $Q_{MAX}$)

iii. $R_1$ range = 0.1 to 1.0 iv. $\Delta T_{inj1}$ range = $\Delta T_{scan}$ to $\Delta T_{scan}$+8 v. $R_2$ range = 0.05 to 0.95 vi. $\Delta T_{inj2}$ range = 0 to $\Delta T_{scan}$ b. Find values for $T^*_{start}$, $Q^*_{inj1}$, $R^*_1$, $\Delta T^*_{inj1}$, $R^*_2$, $\Delta T^*_{inj2}$, which are the arguments that minimize the cost function of Equation (14).

$$T^*_{start}, Q^*_{inj}, R^*_1, \Delta T^*_{inj1}, R^*_2, \Delta T^*_{inj2} = \underset{\substack{T_{start}, Q_{inj}, \\ R_1, \Delta T_{inj1}, \\ R_2, \Delta T_{inj2}}}{\arg\min} \begin{pmatrix} \left|C_{LH\text{-}Peak} - C_{LH\text{-}Peak\text{-}Desired}\right| + \\ \left|C_{LH\text{-}Start} - C_{LH\text{-}Target\text{-}Desired}\right| + \\ \left|C_{LH\text{-}End} - C_{LH\text{-}Target\text{-}Desired}\right| + \\ \alpha\left|C_{RH\text{-}Start} - C_{RH\text{-}Target\text{-}Desired}\right| + \\ \alpha\left|C_{RH\text{-}End} - C_{RH\text{-}Target\text{-}Desired}\right| + \\ \beta\left|Q_{inj} - Q_{TB}\right| + \\ \gamma, if\left(Q_{inj}\left(R_1\Delta T_{inj1} + R_2\Delta T_{inj2}\right) > V_{Load}\right) \end{pmatrix}$$

METHODS FOR DETERMINATION OF PARAMETERS FOR A PROCEDURE, FOR ESTIMATION OF CARDIOPULMONARY FUNCTION AND FOR FLUID DELIVERY

CROSS-REFERENCE TO RELATED APPLICATION

This application is a national stage application of PCT/US2008/67982, filed Jun. 24, 2008, which claims the benefit of U.S. Provisional Patent Application Ser. No. 60/950,148, filed Jul. 17, 2007, the disclosure of which is incorporated herein by reference.

BACKGROUND OF THE INVENTION

The present invention is related to devices, systems and methods for determination of parameters for a procedure, for estimation of cardiopulmonary function and for fluid delivery, and, particularly, to devices, systems and methods for delivery of a pharmaceutical fluid to a patient based upon estimation of cardiovascular function (for example, cardiac output) of the patient, and, especially for delivery of a contrast medium to a patient during a medical injection procedure.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

The administration of contrast medium (with, for example, a powered injector) for radiological exams typically starts with the clinician filling an empty, disposable syringe with a certain volume of contrast agent pharmaceutical. In other procedures, a syringe pre-filled with contrast agent is used. The clinician then determines a volumetric flow-rate and a volume of contrast to be administered to the patient to enable a diagnostic image. An injection of saline solution, having a volume and flow rate determined by the operator, often follows the administration of contrast agent into the veins or arteries. A number of currently available injectors allow for the operator to program a plurality of discrete phases of volumetric flow rates and volumes to deliver. For example, the SPECTRIS SOLARIS® and STELLANT® injectors available from Medrad, Inc. of Indianola, Pa., provide for entry of up to and including six discrete pairs or phases of volumetric flow rate and volume for delivery to a patient (for example, for contrast and/or saline). Such injectors and injector control protocols for use therewith are disclosed, for example, in U.S. Pat. No. 6,643,537 and Published U.S. Patent Application Publication No. 2004-0064041, the disclosures of which are incorporated herein by reference. The values or parameters within the fields for such phases are generally entered manually by the operator for each type of procedure and for each patient undergoing an injection/imaging procedure. Alternatively, earlier manually entered values of volume and flow rate can be stored and later recalled from the computer memory. However, the manner in which such parameters are to be determined for a specific procedure for a specific patient continues to undergo development.

In that regard, differences in contrast dosing requirements for different patients during imaging and other procedures have been recognized. For example, U.S. Pat. No. 5,840,026, the disclosure of which is incorporated herein by reference, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures. Given the increased scan speed of recently available CT scanners including MDCT (or MSCT) scanners, single phase injections are dominant over biphasic or other multiphasic injections in regions of the world where such fast scanners are used. Although using standard, fixed or predetermined protocols (whether uniphasic, biphasic or multiphasic) for delivery simplifies the procedure, providing the same amount of contrast media to different patients under the same protocol can produce very different results in image contrast and quality. Furthermore, with the introduction of the newest MDCT scanners, an open question in clinical practice and in the CT literature is whether the standard contrast protocols used with single-slice, helical scanners will translate well to procedures using the MDCT machines.

A few studies have attempted quantitative analyses of the injection process during CT angiography (CTA) to improve and predict arterial enhancement. For example, Bae and coworkers developed pharmacokinetic (PK) models of the contrast behavior and solved the coupled differential equation system with the aim of finding a driving function that causes the most uniform arterial enhancement. K. T. Bae, J. P. Heiken, and J. A. Brink, "Aortic and hepatic contrast medium enhancement at CT. Part I. Prediction with a computer model," *Radiology*, vol. 207, pp. 647-55 (1998); K. T. Bae, "Peak contrast enhancement in CT and MR angiography: when does it occur and why? Pharmacokinetic study in a porcine model," *Radiology*, vol. 227, pp. 809-16 (2003); K. T. Bae et al., "Multiphasic Injection Method for Uniform Prolonged Vascular Enhancement at CT Angiography: Pharmacokinetic Analysis and Experimental Porcine Method," *Radiology*, vol. 216, pp. 872-880 (2000); U.S. Pat. Nos. 5,583,902, 5,687,208, 6,055,985, 6,470,889 and 6,635,030, the disclosures of which are incorporated herein by reference. An inverse solution to a set of differential equations of a simplified compartmental model set forth by Bae et al. indicates that an exponentially decreasing flow rate of contrast medium may result in optimal/constant enhancement in a CT imaging procedure. However, the injection profiles computed by inverse solution of the PK model are profiles not readily realizable by most CT power injectors without major modification.

In another approach, Fleischmann and coworkers treated the cardiovascular physiology and contrast kinetics as a "black box" and determined its impulse response by forcing the system with a short bolus of contrast (approximating a unit impulse). In that method, one performs a Fourier transform on the impulse response and manipulates this transfer function estimate to determine an estimate of a more optimal injection trajectory than practiced previously. D. Fleischmann and K. Hittmair, "Mathematical analysis of arterial enhancement and optimization of bolus geometry for CT angiography using the discrete Fourier transform," *J Comput Assist Tomogr*, vol. 23, pp. 474-84 (1999), the disclosure of which is incorporated herein by reference.

Uniphasic administration of contrast agent (typically, 100 to 150 mL of contrast at one flow rate) results in a non-uniform enhancement curve. See, for example, D. Fleischmann and K. Hittmair, supra; and K. T. Bae, "Peak contrast enhancement in CT and MR angiography: when does it occur and why? Pharmacokinetic study in a porcine model," *Radi-*

*ology*, vol. 227, pp. 809-16 (2003), the disclosures of which are incorporated herein by reference. Fleischmann and Hittmair thus presented a scheme that attempted to adapt the administration of contrast agent into a biphasic injection tailored to the individual patient with the intent of optimizing imaging of the aorta. A fundamental difficulty with controlling the presentation of CT contrast agent is that hyperosmolar drug diffuses quickly from the central blood compartment. Additionally, the contrast is mixed with and diluted by blood that does not contain contrast.

Fleischmann proscribed that a small bolus injection, a test bolus injection, of contrast agent (16 ml of contrast at 4 ml/s) be injected prior to the diagnostic scan. A dynamic enhancement scan was made across a vessel of interest. The resulting processed scan data (test scan) was interpreted as the impulse response of the patient/contrast medium system. Fleischmann derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level) Fleischmann derived an input time signal by dividing the frequency domain representations of the desired output by that of the patient transfer function. Because the method of Fleischmann et. al. computes input signals that are not realizable in reality as a result of injection system limitations (for example, flow rate limitations), one must truncate and approximate the computed continuous time signal.

In addition to problems of control with current injector systems, many such systems lack convenience and flexibility in the manner in which the injector systems is operated. In that regard, the complexity of medical injection procedures and the hectic pace in all facets of the health care industry place a premium on the time and skills of an operator.

In many current quantitative analysis techniques, clinical practicalities thus diminish the chances of adoption into regular use. Physiological models can require the estimation of many physiologic parameters a priori (for example, cardiac output, organ and great vessel blood volumes, permeability factors). The models may not be well oriented towards per-patient adaptation based on test-bolus enhancement because of certain mathematical limitations. Moreover, methodologies in which an impulse response is determined using a short bolus of contrast can be difficult to implement practically because satisfactory means do not exist to easily transfer time-bolus enhancement data between a scanner and an injection system.

Although advances have been made in the control of fluid delivery systems to, for example, provide a desirable time enhancement curve and to provide for patient safety, it remains desirable to develop improved devices, systems, and method for delivery of fluids to a patient.

SUMMARY OF THE INVENTION

In one aspect, the present invention provides a method of determining at least one parameter for an imaging procedure including the injection of a contrast enhancement fluid which includes a contrast enhancing agent. The method includes substituting into a model discrete point data determined from at least one contrast time enhancement curve measured using an imaging system for a first region of interest resulting from injection of a bolus of the contrast enhancement fluid. In several embodiments, a sufficient number of data points can be substituted into the model to determine values for physiological variables in the model. The variables can, for example, be related to cardiopulmonary function.

In a number of embodiments, at least one data point from at least a second contrast time enhancement curve for a second region of interest measured using the imaging system is substituted into the model.

The at least one parameter can, for example, be a parameter of at least one phase of an injection procedure for the injection of the contrast enhancement fluid or a parameter of the imaging system.

In several embodiments, data from the time enhancement curve of the first region of interest corresponds to a first pass of contrast enhancement fluid through the first region of interest, and data from the time enhancement curve of the second region of interest corresponds to a first pass of contrast enhancement fluid through the second region of interest.

An analyzed portion of the time enhancement curve of the first region of interest can, for example, overlap an analyzed portion of the time enhancement curve of the second region of interest in time. At least one contrast enhancing agent concentration on one of the contrast enhancement curves at a certain time can be related to a contrast enhancing agent concentration on the other of the contrast enhancement curves at the certain time or a time in proximity to the certain time using a conservation of mass balance. In several embodiments, it is assumed that the loss of contrast enhancement fluid between the first region of interest and the second region of interest is negligible. In several embodiments, it is assumed that the blood volume for the first region of interest is equal to the blood volume for the second region of interest.

The model can be a physiological model in which cardiac output and blood volume are variables. Cardiac output and blood volume between the injection site and the measurement point can be calculated for a patient. Subsequently, parameters for a procedure protocol (for example, an imaging procedure) can determined using the physiological model or another model (which can, for example, be a parametric or a nonparametric model). For example, an optimization procedure can be performed to determine one or more parameters.

In several embodiments, a time to peak enhancement for first region of interest enhancement $T_1$ and a time to peak enhancement for the second region of interest enhancement $T_2$ are input. Concentration at peak enhancement for the first region of interest enhancement $C_1(T_1)$ and concentration at peak enhancement for the second region of interest enhancement $C_2(T_2)$ are also input.

The distribution of contrast material injected into each region of interest from a peripheral injection site can, for example, be described by the following analytical solution of a physiological model:

$$C_o(t) = \begin{cases} \frac{Q_{inj}}{Q_{CO}} C_i \left(1 - e^{-\frac{Q_{CO}}{V_B} t}\right) & t \leq T_{inj} \\ C_o(T_{inj}) e^{-\frac{Q_{CO}}{V_B}(t - T_{inj})} & t > T_{inj} \end{cases}$$

wherein the origin, t=0, corresponds to the time at which contrast arrives in the region of interest, $Q_{inj}$ [ml/s] is the injection flow rate, $T_{inj}$ [s] is the injection duration, $Q_{CO}$ is the cardiac output [ml/s], $V_B$ is the blood volume between the injection site and measurement point [ml], $C_i$ is the concentration of contrast in a contrast source from which contrast is injected into the patient, and $C_o(t)$ is the blood concentration in the region of interest of the agent at time t.

Concentration can, for example, be related to enhancement level by the formula:

$$C_O(t) = s(t)/K$$

wherein s(t) [Hounsfield units or HU] is enhancement level at time t and K [mgI/ml] is a conversion factor.

$T_{inj}$ can, for example, be the amount of time between arrival of contrast enhancement agent and the time to peak enhancement.

Blood concentration at $T_{inj}$ can be provided by:

$$C_o(T_{inj}) = \frac{\max s_2(T_2)}{K} = C_2(T_2)$$

wherein max $s_2(T_2)$ [Hu] is the maximum enhancement level in the second region of interest and $C_2(T_2)$ is the concentration at peak enhancement for the second region of interest enhancement.

Contrast enhancing agent concentration on the first contrast enhancement curve at time $T_2$ can be related to a contrast enhancing agent concentration on the second contrast enhancement curves at time $T_2$ using the following equation $$C_1(T_2) \approx C_1(T_1) - C_2(T_2).$$

Blood volume $V_B$ can be determined using one of the following formulas:

$$V_B = \frac{-T_1 Q_{CO}}{\log\left[1 - \frac{C_1(T_1)}{Q_{inj} C_i} Q_{CO}\right]} \quad V_B = \frac{-(T_2 - T_1) Q_{CO}}{\log\left[\frac{C_1(T_1) - C_2(T_2)}{C_1(T_1)}\right]}.$$

Cardiac output $Q_{CO}$ can be determined using the following formula:

$$Q_{CO} = \frac{Q_{inj}}{C(T_1)} C_i \left[1 - \left(\frac{C_1(T_1) - C_2(T_2)}{C_1(T_1)}\right)\right]^{\frac{T_1}{T_2 - T_1}}.$$

$Q_{CO}$ can be used in the model in which $Q_{CO}$ is a variable to determine the at least one parameter.

The concentration of contrast agent at peak enhancement $C(T_{Peak})$ (sometimes written herein simply as $C_{Peak}$) at the time of peak enhancement $T_{Peak}$ in the second region of interest of an imaging injection can be related to the injection flow rate $Q_{inj}$ of the imaging injection and the injection duration $T_{inj}$ of the imaging injection using the formula:

$$C(T_{Peak}) = \frac{Q_{inj}}{Q_{CO}} C_i \left[1 - e^{-\frac{Q_{CO}}{V_B} T_{inj}}\right]$$

A concentration of contrast agent in the second region of interest at time of a scan start, $C(T_{start})$ (sometimes written herein simply as $C_{start}$), can be provided by:

$$C(T_{Start}) = \frac{\frac{Q_{inj}}{Q_{CO}} C_i \left[1 - e^{-\frac{Q_{CO}}{V_B} T_{inj}}\right]}{1 - e^{-\frac{Q_{CO}}{V_B} T_{inj}} + e^{-\frac{Q_{CO}}{V_B}(T_{inj} - \Delta T)}}$$

wherein $\Delta T$ is the scan duration and wherein $C(T_{start})$ is equal to $C(T_{start} + \Delta T)$.

$C(T_{Peak})$ and $C(T_{start})$ enhancements can, for example, be determined for admissible input values for $T_{inj}$ and $Q_{inj}$ wherein a maximum $Q_{inj}$ and a minimum $Q_{inj}$ and a maximum $T_{inj}$ and a minimum $T_{inj}$ can be established. Maximum $T_{inj}$ can, for example, be established as a function of scan duration plus a constant, and minimum $T_{inj}$ can, for example, be established as the scan duration.

The values for the diagnostic protocol flow rate $Q^*_{inj}$ and injection duration $T^*_{inj}$ can, for example, be determined which are the arguments that minimize the cost function:

$$Q^*_{inj}, T^*_{inj} = \underset{Q_{inj}, T_{inj}}{\operatorname{argmin}}(|DesiredPeak - C(T_{Peak})| + |DesiredTarget - C(T_{start})|).$$

In another embodiment, wherein the first region of interest is a region of interest indicative or concentration/enhancement in the right heart (for example, the pulmonary artery) and the second region of interest is a region of interest indicative or concentration/enhancement in the left heart (for example, the ascending aorta), values for the diagnostic protocol flow rate can be determined which are the arguments that minimize the cost function:

$$T^*_{start}, Q^*_{inj}, R^*_1, \Delta T^*_{inj1}, R^*_2, \Delta T^*_{inj2} = \underset{\substack{T_{start}, Q_{inj}, \\ R_1, \Delta T_{inj1}, \\ R_2, \Delta T_{inj2}}}{\operatorname{argmin}} \begin{pmatrix} |C_{LH-Peak} - C_{LH-Peak-Desired}| + \\ |C_{LH-Start} - C_{LH-Target-Desired}| + \\ |C_{LH-End} - C_{LH-Target-Desired}| + \\ \alpha |C_{RH-Start} - C_{RH-Target-Desired}| + \\ \alpha |C_{RH-End} - C_{RH-Target-Desired}| + \\ \beta |Q_{inj} - Q_{TB}| + \\ \gamma, \text{if}(Q_{inj}(R_1 \Delta T_{inj1} + R_2 \Delta T_{inj2}) > V_{Load}) \end{pmatrix}$$

wherein $T_{start}$ is a time of start of a scan, $R_1$ is a rate of injection in a phase wherein only contrast medium is injected, $\Delta T_{inj1}$ is the time of duration of the phase wherein only contrast medium is injected, $R_2$ is a rate of injection in a phase wherein contrast medium and diluent are injected, $\Delta T_{inj2}$ is the time of duration of the phase wherein contrast medium and diluent are injected, $C_{LH-Peak}$ is a calculated concentration at peak enhancement in the left heart, $C_{LH-Desired}$ is a desired concentration at peak enhancement in the left heart, $C_{LH-Start}$ is a calculated concentration in the left heart at the time of start of the scan, $C_{LH-Target-Desired}$ is a desired concentration in the left heart at the time of start of the scan, $C_{LH-End}$ is a calculated concentration in the left heart at the time of the end of the scan or $T_{End}$, $C_{RH-Start}$ is a calculated concentration in the right heart at the time of start of the scan, $C_{RH-Target-}$ $_{Desired}$ is a desired concentration in the right heart at the time of start of the scan, and $C_{RH-End}$ is a calculated concentration in the right heart at the time of the end of the scan, α is a weighting factor, β is a weighting factor and γ is a penalty. γ can, for example, be a defined value if $(Q_{inj}(R_1\Delta T_{inj1}+R_2\Delta T_{inj2})>V_{Load})$ is true (for example, 1000) and can be 0 if $(Q_{inj}(R_1\Delta T_{inj1}+R_2\Delta T_{inj2})>V_{Load})$ is not true, wherein $V_{Load}$ is the total volume of contrast available.

$C_{LH-Peak}$ can, for example, be the greater of the value calculated as follows:

$$C_{LH-Peak} = \frac{Q_{inj}}{Q_{CO}} C_i R_1 \left(1 - e^{-\frac{Q_{CO}}{V_B}\Delta T_{inj1}}\right) \text{ or}$$

$$C_{LH-Peak} = \frac{Q_{inj}}{Q_{CO}} C_i R_1 \left(1 - e^{-\frac{Q_{CO}}{V_B}\Delta T_{inj1}}\right) e^{-\frac{Q_{CO}}{V_B}\Delta T_{inj2}} + \frac{Q_{inj}}{Q_{CO}} C_i R_2 \left(1 - e^{-\frac{Q_{CO}}{V_B}\Delta T_{inj2}}\right)$$

The concentration $C_T$ in the right heart or the left heart as applicable at a time T, which is either $T_{start}$ or $T_{end}$, when $T<(T_{arr}+\Delta T_{inj1})$, wherein $T_{arr}$ is either the time of arrival of contrast at the right heart or at the left heart as applicable, can be calculated by the following formula:

$$C_T = \frac{Q_{inj}}{Q_{CO}} C_i R_1 \left(1 - e^{-\frac{Q_{CO}}{V_B}(T-T_{arr})}\right).$$

The concentration $C_T$ in the right heart or the left heart as applicable at a time T, when, $(T_{arr}+\Delta T_{inj1})<T<(T_{arr}+\Delta T_{inj1}+\Delta T_{inj2})$ can be calculated by the following formula:

$$C_T = \frac{Q_{inj}}{Q_{CO}} C_i R_1 \left(1 - e^{-\frac{Q_{CO}}{V_B}\Delta T_{inj1}}\right) e^{-\frac{Q_{CO}}{V_B}(T-(T_{arr}+\Delta T_{inj1}))} + \frac{Q_{inj}}{Q_{CO}} C_i R_2 \left(1 - e^{-\frac{Q_{CO}}{V_B}(T-(T_{arr}+\Delta T_{inj1}))}\right)$$

The concentration $C_T$ in the right heart or the left heart as applicable at a time T, when $T>(T_{arr}+\Delta T_{injA}+\Delta T_{injAB})$, can be calculated by the following formula:

$$C_T = \left(\begin{array}{c}\frac{Q_{inj}}{Q_{CO}} C_i R_1 \left(1 - e^{-\frac{Q_{CO}}{V_B}\Delta T_{inj1}}\right) e^{-\frac{Q_{CO}}{V_B}\Delta T_{inj2}} + \\ \frac{Q_{inj}}{Q_{CO}} C_i R_2 \left(1 - e^{-\frac{Q_{CO}}{V_B}\Delta T_{inj2}}\right)\end{array}\right)$$

$$e^{-\frac{Q_{CO}}{V_B}(T-(T_{arr}+\Delta T_{inj1}+\Delta T_{inj2}))}$$

In another aspect, the present invention provides a parameter generation system to determine at least one parameter for a procedure including injection of a contrast enhancement fluid which includes a contrast enhancing agent adapted to enhance contrast in an imaging system. The system includes an input system to receive point data from at least a first time enhancement curve from a first region of interest resulting from injection of a test bolus and at least one processor in communicative connection with the input system to determine the at least one parameter based at least in part upon substitution of the point data into a model. As described above, a sufficient number of data points can be substituted into the model to determine values for physiological variables in the model. The variables can, for example, be related to cardiopulmonary function.

At least one data point from at least a second contrast time enhancement curve measured using the imaging system in at least a second region of interest can also be input into the input system and substituted into the model.

The at least one parameter can, for example, be a parameter of at least one phase of an injection procedure for the injection of the contrast enhancement fluid or a parameter of the imaging system.

Data from the time enhancement curve of the first region of interest can correspond to a first pass of contrast enhancement fluid through the first region of interest, and data from the time enhancement curve of the second region of interest can correspond to a first pass of contrast enhancement fluid through the second region of interest.

An analyzed portion of the time enhancement curve of the first region of interest can, for example, overlap an analyzed portion of the time enhancement curve of the second region of interest in time. At least one contrast enhancing agent concentration on one of the contrast enhancement curves at a certain time can be related to a contrast enhancing agent concentration on the other of the contrast enhancement curve at the certain time or a time in proximity to the certain time using a conservation of mass balance.

In several embodiments, it is assumed that the loss of contrast enhancement fluid between the first region of interest and the second region of interest is negligible.

In another aspect, the present invention provides an injector system including a parameter generation system to determine at least one parameter for a procedure including injection of a contrast enhancement fluid which includes a contrast enhancing agent adapted to enhance contrast in an imaging system. The parameter generation system includes an input system to input/receive (either manually or in an automated, electronically communicated manner) point data from at least a first time enhancement curve from a first region of interest resulting from injection of a test bolus and at least one processor in communicative connection with the input system to determine the at least one parameter based at least in part upon substitution of the point data into a model.

In a further aspect, the present invention provides a system including an injector system, an imaging system and parameter generation system to determine at least one parameter for a procedure including injection of a contrast enhancement fluid which includes a contrast enhancing agent adapted to enhance contrast in an imaging system. The parameter generation system includes an input system to input/receive point data from at least a first time enhancement curve from a first region of interest resulting from injection of a test bolus and at least one processor in communicative connection with the input system to determine the at least one parameter based at least in part upon substitution of the point data into a model.

In still a further aspect, the present invention provides a method of determining at least one parameter for a procedure, including: substituting into a model discrete point data determined from at least one time concentration curve measured using a sensor for at least a first region of interest resulting from injection of a bolus of the a pharmaceutical. A sufficient number of data points can be substituted into the model to determine values for physiological variables in the model. The variables can, for example, be related to cardiopulmonary function. At least one data point from at least a second contrast time enhancement curve for a second region of interest can be measured and substituted into the model.

As used herein with respect to an injection procedure, the term "protocol" refers generally to a group of parameters for a procedure (for example, an imaging procedure involving the injection of a contrast enhancement fluid or contrast medium) Injection parameter can, for example, include as flow rate, volume injected, injection duration, contrast agent concentration etc. that define, for example, the timing of, amount of, and/or the nature of fluid(s) to be delivered to a patient during an injection procedure. Such parameters can change over the course of the injection procedure. As used herein, the term "phase" refers generally to a group of parameters that define, for example, the timing of, amount of, and/or the nature of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can, for example, be described as uniphasic (a single phase), biphasic (two phases) or multiphasic (two or more phases, but typically more than two phases). Multiphasic injections also include injections in which the parameters can change continuously over at least a portion of the injection procedure.

Scanner parameters that can be determined include, but are not limited to, the amount of radiation transmitted to the patient, power inputs (for example, voltage or current), timing (for example, scan start time, stop time, delay time and/or duration).

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 10B illustrates data obtained in a study group of 70 patients scheduled for clinically indicated dual source CT or DSCT studies under one embodiment of the present invention

FIG. 10F illustrated mean attenuation for each of the control group and the study group for each of the anatomical regions studied.

DETAILED DESCRIPTION OF THE INVENTION

Figure 1:
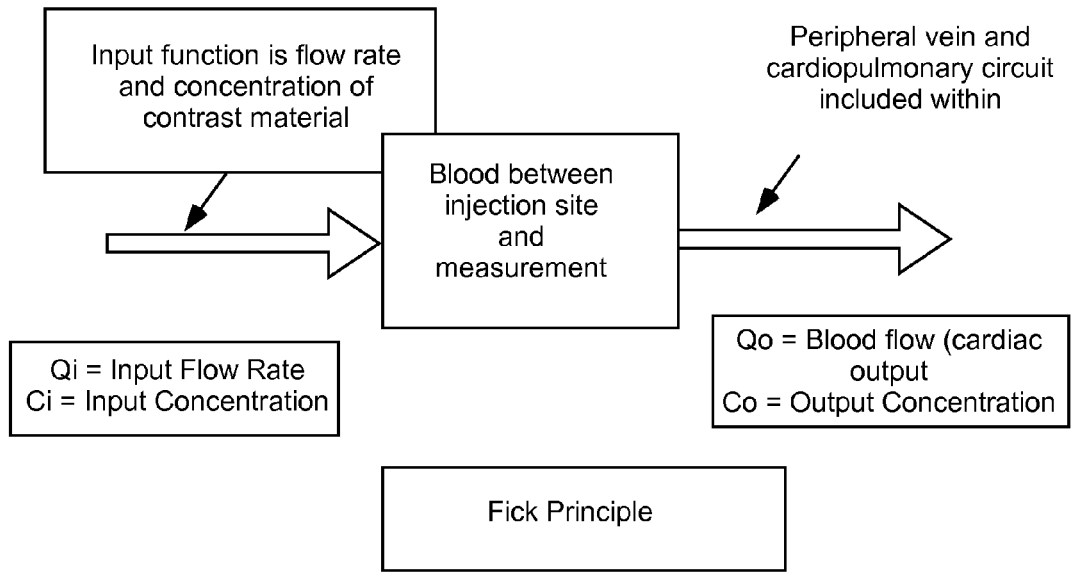
FIG. 1 illustrates a schematic representation of a Fick Principles model used in several embodiment of fluid delivery systems and methods of the present invention.

In the present invention, variables in a model that is predictive of temporal changes in concentration in a region or regions of interest within a patient are determined or estimated using data from at least one concentration profile for a pharmaceutical (that is, concentration as a function of time) in at least one region of interest. Depending upon the number of variables present within the model, a number of discrete data points are taken from one or more contrast concentration profiles (that are, for example, provided by time enhancement curves generated using an imaging system) to provide an estimation of the values of such variables. In a number of models, such variables are related to cardiopulmonary function (that is, cardiac, pulmonary and vascular function/dynamics). For example, in a representative embodiment of a model used in the present invention, two variables, cardiac output ($Q_{CO}$) and blood volume ($V_B$), are unknown. Two discrete data points (that is, two concentrations at two times) are used to determine estimates of those variable.

In the case of imaging systems or scanners currently in use, it can be difficult (for example, as a result of noise in the signal or other difficulty in reading/determining data points from the imaging system) to accurately determine multiple data points upon one or more time enhancement curves. However, in a number of models, it is relatively straightforward to determine, for example, a peak enhancement and an associated time to peak enhancement. Indeed, software associated with such systems is often optimized to determine peak enhancement and time to peak enhancement.

In several embodiments of the present invention, an estimation of model variables (for example, variables related to cardiopulmonary function) is made upon analysis of at least two concentration profiles of a pharmaceutical as a function of time and using point data from such concentration profiles to determine variables as described above. In a number of such embodiments, concentration profiles at more than one region of interest are related and the concentrations and times associated with the peak concentrations are used to determine variables in a model as described above. For example, in the case of a model including two physiological variables, peak enhancements/concentrations and times to peak enhancement for a first region of interest (that is, location within the body of a patient) and for at least a second region of interest can be used to determine the variables.

One skilled in the art appreciates that the analysis can be performed in association with generally any type of pharmaceutical in connection with an appropriate sensor system to measure concentration profiles of the pharmaceutical at two or more locations or regions of interest within the body. The combination of injection of a contrast enhancing fluid and the use of an imaging system to measure enhancement/concentration at a plurality of regions of interest provides an effective and minimally invasive technique for estimation of, for example, cardiovascular function in the present invention, and the combination or contrast injection/CT image scanning is discussed as a representative example herein. Once an estimation of cardiovascular parameters (for example, cardiac output, blood volume etc.) is made those parameters can be used in determining parameters for any number of procedures including, for example, parameters for therapeutic drug delivery, parameters for an imaging procedure etc.

In the case of injection of a contrast enhancement fluid, a suitable analysis of a full test-bolus time enhancement curve (sometimes referred to herein simply an enhancement curve) may enable the full estimation of cardiopulmonary and vascular parameters necessary for developing optimal contrast injections. However, such methodologies are limited, for example, because satisfactory means do not exist to easily transfer time-bolus enhancement data between a scanner and an injection system. Although sharing of a complete time-enhancement curve between a scanner and an injection system for analysis therein is not currently implemented in available scanners and injectors, intermediate algorithmic options can still incorporate data accessible from time-bolus enhancement curves. Such data can, for example, provide the best available indication of a patient's cardiovascular dynamics. In the systems and method of PCT International Patent Application No. PCT/US2007/026194, the disclosure of which is incorporated herein by reference, iodine administration rate of contrast agent/material is adjusted based on the patient's weight and a scan duration. See also Published PCT Application Nos. WO/2006/058280 and WO/2006/055813, the disclosures of which are incorporated herein by reference. Further refinement of the determined diagnostic injection protocol is made based on the peak enhancement value and time to peak of a test bolus enhancement curve in the patient's ascending aorta/aortic arch. That data from the time-enhancement curve are used in protocol generation to determine the scan delay, to determine the dilution ratio and thus Iodine administration rate of a second, dual-flow phase (in which contrast media and a diluent are simultaneously injected), and to determine at what point the injection system should stop injecting to prevent excess injection (for that patient) of contrast material. That methodology has shown promise in reducing the dependency of contrast enhancement on patient habitus, better consistency of right ventricle enhancement, and easing technologist workflow during the execution of personalized injection protocols. That methodology can be further optimized if one relaxes the constraint of eliminating contrast residual and allows for the manipulation of flow rates after the test bolus has been administered.

It is well known that cardiac output and vascular blood volume are important parameters affecting contrast bolus propagation. If the entire time enhancement curve from a test bolus is available, robust and reliable estimates of these parameters can be made in a parametric or non-parametric paradigm. Requiring a technologist to manually enter all or even more than 4 points from a time enhancement curve can be overly taxing. However, there is insufficient useful information from the peak concentration and time to peak of only a single test bolus curve to make a quantitative estimate of cardiac output (beyond stating that an inverse relationship exists between the peak enhancement and cardiac output).

Use of regression formulae with weight, scan duration, concentration and test bolus enhancement data to calculate cardiac output and vascular blood volume is also less than optimal. For example, the regression coefficients generated from one set of data are not necessarily valid for predicting a treatment response of another group. A simple nomogram can also be generated, the heuristics of which map test bolus enhancement data to injection flow rate. Another approach is to estimate the total blood volume from look-up table relationships and divide by a factor to consider only the volume between the injection point and, for example, the cardiac anatomy. These classes of algorithms are less than optimal, however, because they are not predicated on physical principles, are not robust to variations in parameter and measurement uncertainty, and are difficult to validate. Furthermore, those algorithms do not provide for easy manipulation of other injection parameters such as dilution ratio of contrast/saline, scan delay, and injection duration of contrast material.

As described above, in several embodiments, the systems and methods of the present invention provide data-driven, parametric estimation techniques that use, for example, the times to peak and peak concentrations/enhancements of at least two time concentration/enhancement curves (each for a different region of interest or ROI) generated, for example, from a test or timing bolus (or injection) to estimate the subject's cardiac output and blood volume between, for example, the injection site and cardiac anatomy. As clear to one skilled in the art, more than two ROIs can be use in the estimation techniques of the present invention.

The estimations of physiological variables (for example, cardiac output and/or blood volume) are used in a model such as a pharmacokinetic model to determine suitable injection parameters to, for example, achieve a desired enhancement in a region of interest. The same model via which the physiological parameters were determined can, for example, be used to determine protocol parameters (for example, injection parameters and/or imaging/scanning parameters). Alternatively or additionally, the variables can be used in connection with at least one other model (which can, for example, be a parametric model or a nonparametric model) to determine protocol parameters. Various models are, for example, discussed in PCT International Patent Application No. PCT/US2007/026194 and in Published PCT Application Nos. WO/2006/058280 and WO/2006/055813. In a number of embodiments, for example, an optimized protocol generation algorithm, computes a flow rate, an injection duration and/or other parameters to achieve predetermined enhancement levels throughout the scan duration using the determined physiological variables (for example, estimated cardiac output and blood volume) as input.

In several embodiments, the first ROI (during the timing bolus procedure) occurs first in the circulation of the injected contrast enhancing fluid (that is, it is closest in the circulation path to the injection site) and the second ROI is the ROI of primary interest in the imaging procedure. However, injection parameters can be determined to effect a desired enhancement in either or both the first and second ROIs (or one or more other ROIs). In general, the ROIs used in the parametric estimation techniques can be relatively close to each other in the blood circulation path such that the first pass enhancement curves overlap each other over at least a portion of the enhancement curves. The techniques of the present invention are, for example, well suited for ROIs that are within blood vessels such as in the case of angiography studies. However, the techniques of the present invention are also suitable for use in connection with tissue (such as studies of tumor uptake).

In several representative studies of the present invention, a first time enhancement curve was generated with an ROI in, for example, the pulmonary trunk and a second time enhancement curve was generated from an ROI in the ascending aorta. The data were, for example, generated from serial computed tomography or CT scanning at the level of the pulmonary trunk starting, for example, 4-5 seconds after the start of contrast injection. One skilled in the art appreciates that the systems and methods of the present invention are applicable in imaging techniques other than CT, including, but not limited to, magnetic resonance imaging (MRI) scans, Positron Emission Tomography (PET) scans and Single Photon Emission Computed Tomography (SPECT) scans. Likewise, one skilled in the art appreciates, that many different regions of interest can be used as the first and second regions of interest. For example, a first ROI and second ROI can be the femoral artery and the popliteal vein in the legs for the performance of peripheral angiography. In the case of neuro-CT Angiography, any of the basilar arteries and corresponding draining veins can be used as ROIs during the first pass of contrast material. The ROIs need not be limited to ROIs that can be imaged, for example, in a single scan plane. The use of wide volume scanning (for example, wide volume CT scanning) can enable the use of ROIs from various planes within the body.

In several embodiments, systems and methods of the present invention were based, at least in part, upon a one compartment, open pharmacokinetic (PK) model. Such a model can, for example, be suitable for use in modeling first-pass dynamics in, for example, CT angiography of cardiovascular structures. The input to the PK model was the concentration of the contrast medium, flow rate and duration of the injection. In using times to peak and peak enhancement of two time enhancement curves to derive an estimate of the cardiac output and blood volume between the injection site and, for example, the aortic root, a linear relationship between measured enhancement in Hounsfield units (HU) and contrast blood concentration and conservation of mass between the two parts of the cardiopulmonary circuit were assumed. Once an estimate of cardiac output was made, it can, for example, be substituted into the analytic solution of the PK model (and/or used in connection with one or more other models) to determine parameters for an imaging procedure. In several embodiments, a minimal flow rate and injection duration to achieve a desired peak enhancement and desired target enhancements (defined as the HU level that should be attained at the beginning and end of the scan) were determined.

After determining a minimal injection duration that achieves a desired enhancement (for example, defined peak and target enhancement goals), the time at which the scan should start was deduced using the solution of the PK model. In a number of embodiments, a constraint was the enforced that ends the injection of contrast a defined amount of time (for example, 5 seconds) before the scan is done. The actual offset from the end of the scan was, for example, be determined from the time to peak of the pulmonary artery time enhancement curve of the timing bolus procedure, which was assumed to be an indicator of propagation time from the injection site to the right heart. Finally, a per-person dual-flow (dilution) phase was computed given the knowledge of the transit time to the right heart. The transit time was factored into determining the time at which dilution was "cut over". For simplicity, a fixed ratio of 40/60 (contrast/saline) was applied in several representative studies. Techniques for determining a contrast/saline ratio based upon patient specific data which can be used in connection with the present invention are described, for example, in PCT International Patent Application No. PCT/US2007/026194. Moreover, as discussed further below, dilution ratio can be treated as a variable in an optimization procedure in several embodiments of the present invention.

The following expression describes the distribution of contrast material injected into a central blood compartment from a peripheral injection site. The origin, t=0, corresponds to the time at which the contrast material arrives in the region of interest (assuming plug flow of the species):

$$C_o(t) = \begin{cases} \dfrac{Q_{inj}}{Q_{co}} C_i \left(1 - e^{-\frac{Q_{CO}}{V_B}t}\right) & t \leq T_{inj} \\ C_o(T_{inj}) e^{-\frac{Q_{CO}}{V_B}(t-T_{inj})} & t > T_{inj} \end{cases} \quad (1)$$

wherein $Q_{inj}$ [ml/s] is the injection flow rate, $T_{inj}$ [s] is the injection duration, $Q_{CO}$ is the cardiac output [ml/s], $V_B$ is the blood volume between the injection site and measurement point [ml], $C_i$ is the concentration of contrast enhancing agent (for example, iodine) in a source of contrast fluid to be delivered to the patient, and $C_o(t)$ is the blood concentration of the contrast enhancing agent at time t. FIG. 1 graphically depicts this model.

Figure 3:
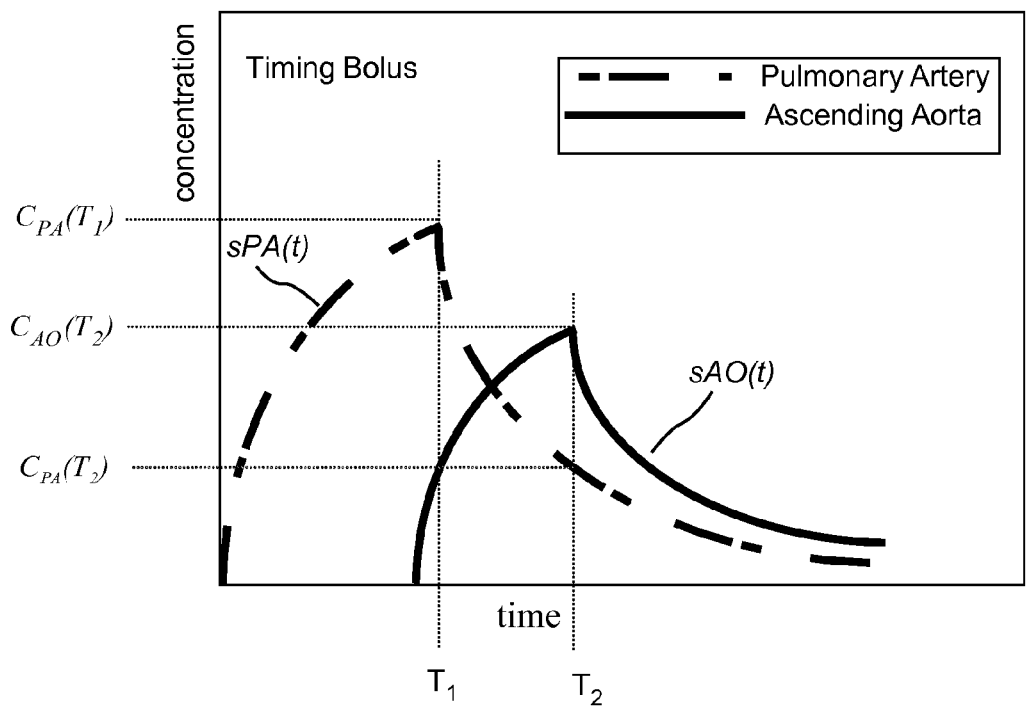
FIG. 3 illustrates sample concentration curves for a timing or test bolus, wherein times to peak and peak enhancements are labeled, and the concentration at a second point ($C_{PA}(T_2)$) on the pulmonary artery (PA) curve is approximated by the difference in peaks.

As, for example, illustrated in FIG. 3, a time enhancement curve $s_{AO}(t)$ [Hounsfield units or HU] measured in a first ROI, the ascending aorta (AO), results from a timing bolus injection. A time enhancement curve $s_{PA}(t)$ [Hounsfield units or HU] measured in a second ROI, the pulmonary artery (PA) trunk, also results from the timing bolus injection. In accordance with the result of previous experimental studies, $T_{inj}$ (the injection duration) is the time to peak enhancement as a result of the timing bolus injection. $K_{HU-mgI}$ is the conversion factor relating HU to concentration of Iodine in vivo at the measurement location. The relationship, then, converting the measured timing bolus enhancement curve in the ascending aorta to concentration units [mgI/ml] is thus:

$$C_o(T_{inj}) = \frac{\max(s_{AO}(t))}{K_{HU\_mgI}} \equiv C_{Peak} \quad (2)$$

A default value for the conversion factor $K_{Hu\_mgI}$ of 25 was used. This value is within the range of 21-26 published by several investigators. Variation in this constant can arise between scanners. Thus, an individual scanner generated calibration curve may be warranted in certain situations.

Estimating Cardiac Output from Timing Bolus Point Data

As described above, in using the governing model to compute a patient-specific diagnostic protocol (including, for example, flow rate and injection duration), estimates of cardiac output ($Q_{CO}$) and blood volume between the injection site and measurement point ($V_B$) were made. Data obtained from the timing bolus enhancement curves, where the flow rate and injection duration are known, were used to solve for these two unknowns.

Ideally, an entire concentration curve would be available to determine a best fit for $Q_{CO}$ and $V_B$. At this time, however, only discrete data point values such as peak enhancements and times to peak in, for example, two structures (for example, the pulmonary artery and the ascending aorta) are reasonably acquired from the timing bolus data. There is, therefore, only one data point on each concentration curve, and the system is underdetermined. The acquisition of two points on a single curve is approximated in the present invention by combining the data points on the individual curves from each structure.

In several embodiments, a number of simplifying assumptions were made. First, it is assumed the blood volumes are the same in both compartments, so that the concentration is directly related to the mass of iodine in the compartment. Without a relationship between the blood volumes in the compartments, the system is still underdetermined with two equations and three unknowns. Second, the system is simplified to two single compartment models where the peak enhancements and times to peak are measured (see FIG. 2A). In this simplification, the contrast is injected, flows into the pulmonary artery, flows into the ascending aorta, and then flows out.

Loss of iodine in an intermediate compartment (such as the lungs) is ignored. Alternatively, a simple relation can be set forth for such loss, without introducing additional variables into the model. Given a lack of enhancement data or volume information available for the intermediate compartments on a per-patient basis and the temporal resolution at which the timing bolus data are acquired, more comprehensive models were not attempted for this computation. The simplified model yields $C_o(t)$ curves similar to those set forth in FIG. 3.

The available measurements are $C_{PA}(T_1)$, $T_1$, $C_{AO}(T_2)$, and $T_2$. At $t=T_1$, $C_{PA}(T_1)/V_B$ ml of iodine are present in the pulmonary artery. This amount of iodine is less than the amount in the test bolus because some has already flowed into the ascending aorta. At $t=T_2$, $C_{AO}(T_2)/V_B$ of iodine are present in the ascending aorta, and there is also some amount of iodine remaining in the pulmonary artery. The shorter peak in the ascending aorta at $T_2$, as compared to the peak for the pulmonary artery, is a result of the iodine left in the previous compartment. Therefore, the second point on the $C_o(t)$ curve for the pulmonary artery, $C_{PA}(T_2)$, can be approximated by the difference in peaks as set forth in Equation (3) below.

$$C_{PA}(T_2) \approx C_{PA}(T_1) - C_{AO}(T_2) \quad (3)$$

As before, the peak of the pulmonary artery curve is defined by:

$$C_{PA}(T_1) = \frac{Q_{inj}}{Q_{CO}} C_i \left(1 - e^{\frac{-Q_{CO}}{V_B} T_1}\right) \quad (4)$$

The expression for $C_{2PA}$ on the downslope is then:

$$C_{PA}(T_2) \approx C_{PA}(T_1) - C_{AO}(T_2) = C_{PA}(T_1)\left(e^{\frac{-Q_{CO}}{V_B}(T_2-T_1)}\right) \quad (5)$$

Rearranging the latter two equations and solving for $V_B$ yields:

$$V_B = \frac{-T_1 Q_{CO}}{\log\left(1 - \frac{C_{PA}(T_1)}{Q_{inj} C_i} Q_{CO}\right)} \quad V_B = \frac{-(T_2 - T_1) Q_{CO}}{\log\left(\frac{C_{PA}(T_1) - C_{AO}(T_2)}{C_{PA}(T_1)}\right)} \quad (6)$$

By equating these two expressions, one can isolate $Q_{CO}$ as follows:

$$Q_{CO} = \frac{Q_{inj}}{C_{PA}(T_1)} C_i \left(1 - \left(\frac{C_{PA}(T_1) - C_{AO}(T_2)}{C_{PA}(T_1)}\right)^{\frac{T_1}{T_2-T_1}}\right) \quad (7)$$

This method fails if $C_{PA}(T_1) < C_{AO}(T_2)$ (the second peak is larger than the first peak), which should only happen when the scan is started too late and the first peak is missed. Despite the simplifying modeling assumptions made, cardiac output estimates were found to be within a reasonable range when both peaks are captured in the scan window.

Diagnostic Injection Protocol Generation—Methodology 1

Figure 2A:
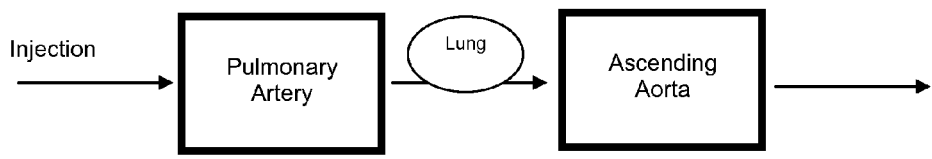
FIG. 2A illustrates a simplified model of contrast injection.
Figure 2B:
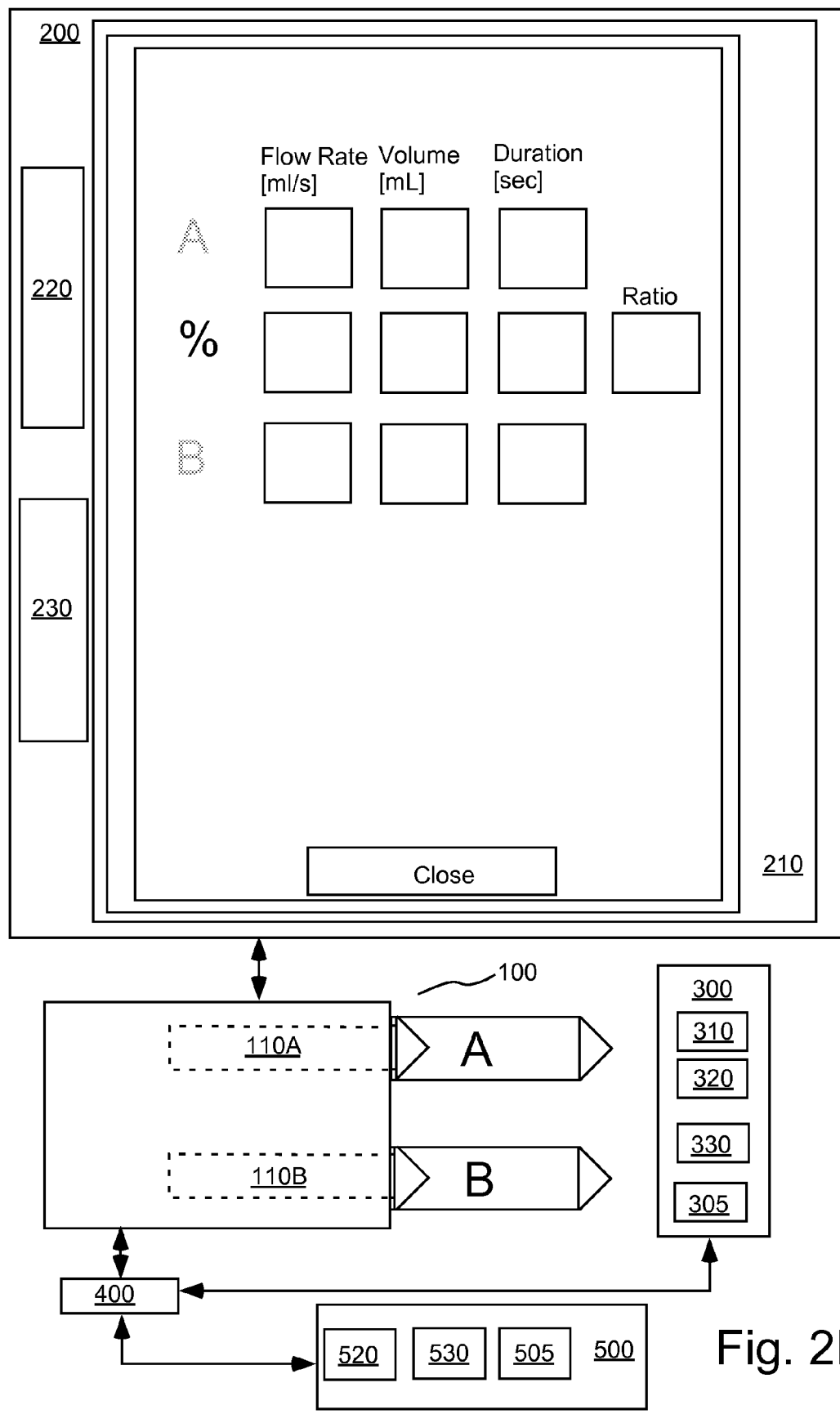
FIG. 2B illustrates an injection system and imaging system of the present invention and a graphical user interface for use in connection with the injection system setting forth areas for parameters for injection flow rate, injection volume and injection duration for, for example, three phase of injection fluids A and B.

In several embodiments of the present invention, an injection system (such as a dual syringe injector system 100 as illustrated in FIG. 2B and as, for example, disclosed in U.S. Pat. No. 6,643,537, Published U.S. Patent Application Publication No. 2004-0064041 and PCT International Patent Application No. PCT/US2007/026194) for use with the present invention includes two fluid delivery sources (sometimes referred to as source "A" and source "B" herein; such as syringes) that are operable to introduce a first fluid and/or a second fluid (for example, contrast enhancement fluid, saline etc.) to the patient independently (for example, simultaneously, simultaneously in different volumetric flow proportion to each other, or sequentially or subsequent to each other (that is, A then B, or B then A)). In the embodiment of FIG. 2A, source A is in operative connection with a pressurizing mechanism such as a drive member 110A, and source B is in operative connection with a pressurizing mechanism such as a drive member 110B. The injection system includes a control system 200 in operative connection with injector system 100 that is operable to control the operation of drive members 110A and 110B to control injection of fluid A (for example, contrast medium) from source A and injection of fluid B (for example, saline) from source B, respectively. Control system 200 can, for example, include or be in communication with a user interface comprising a display 210. In the illustrated embodiment of FIG. 2B, a portion of one embodiment of a screen display is illustrated which shows areas for parameters for injection flow rate, injection volume and injection duration for, for example, three phases of injection of fluid A and/or fluid B. The parameters for one or more such phases can be populated using the parameter generation systems and methods of the present invention. FIG. 2C illustrates another embodiment of a screen display for an embodiment of a system of the present invention as discussed below (methodology 1).

A user can be provided with the option to adjust and/or override the parameters generated (for example, via a manual input system 205 including a keypad, keyboard, mouse etc. as known in the computer arts). Control system 200 can include a processor 220 (for example, a digital microprocessor as known in the art) in operative connection with a memory or memory system 230.

As clear to one skilled in the art, may fluid delivery systems, including multi-patient fluid delivery systems as, for example, disclosed in U.S. Pat. Nos. 7,326,186, 7,094,216, 6,866,654, 6,972,001, 6,699,219, 6,471,674, 6,306,117, 6,149,627, 6,063,052, 5,920,054, 5,843,037, 5,827,219, 5,739,508 and 5,569,181 are also suitable for use in the present invention.

Imaging system 300 can, for example, be a CT system, a Magnetic Resonance Imager (MRI) system, an ultrasound imaging system, or a Positron Emission Tomography (PET) system) or a Single Photon Emission Computed Tomography (SPECT) system as described above. The injection system can be in communicative connection with imaging system 300. Imaging system 300 and injector system 100 can, for example, be in communication connection via input/output ports (represented by terminations of arrows in FIG. 2B) as known in the art. In FIG. 2B, imaging system 300 and injector system 100 are, for example, illustrated to be in communicative connection via a common communication hub 400. Alternatively, a direct communication link can be established. Further data from one of imaging system 300 and injection systems 100 can be manually entered using one or more manual input systems (for example, keypads, keyboards mouse etc.) as know in the computer arts. Imaging system 300 and injector system or injector 100 can also be partially or fully integrated as described, for example, in Published PCT International Patent Application No. WO 2008/011401, the disclosure of which is incorporated herein by reference. One, a plurality or all the illustrated components of the injection system and imaging system 300 can also or alternatively be integrated with or incorporated within another, separate component that is placed in communicative connection with other system components.

Software embodying the systems and methods of the present invention can, for example, be embodied within one or more separate or standalone systems represented by system 500 which can, for example, include at least one processor (for example, a digital microprocessor), a memory system 520 a display 510 and a manual input system 505. In the embodiment illustrated in FIG. 2B, system 500 is shown to be in communicative connection with communication hub 400. As described above, a direct communication link can also be established. Further data from one or more systems can be manually entered into one or more other systems using one or more manual input systems (for example, keypads, keyboards, a mouse etc.) as know in the computer arts. Software embodying the systems and methods of the present invention (including, for example, one or more executable computer algorithms therefor) can, for example, be stored in memory 530 and executed by processor 520. As clear to one skilled in the art, all or a portion of the functionality of the methods and/or systems of the present invention can alternatively reside in an imaging system 300 (which can, for example, include at least one processor 320, a memory system 330, a display 310 and a manual input system 305) and/or in injector system 100.

Figure 4:
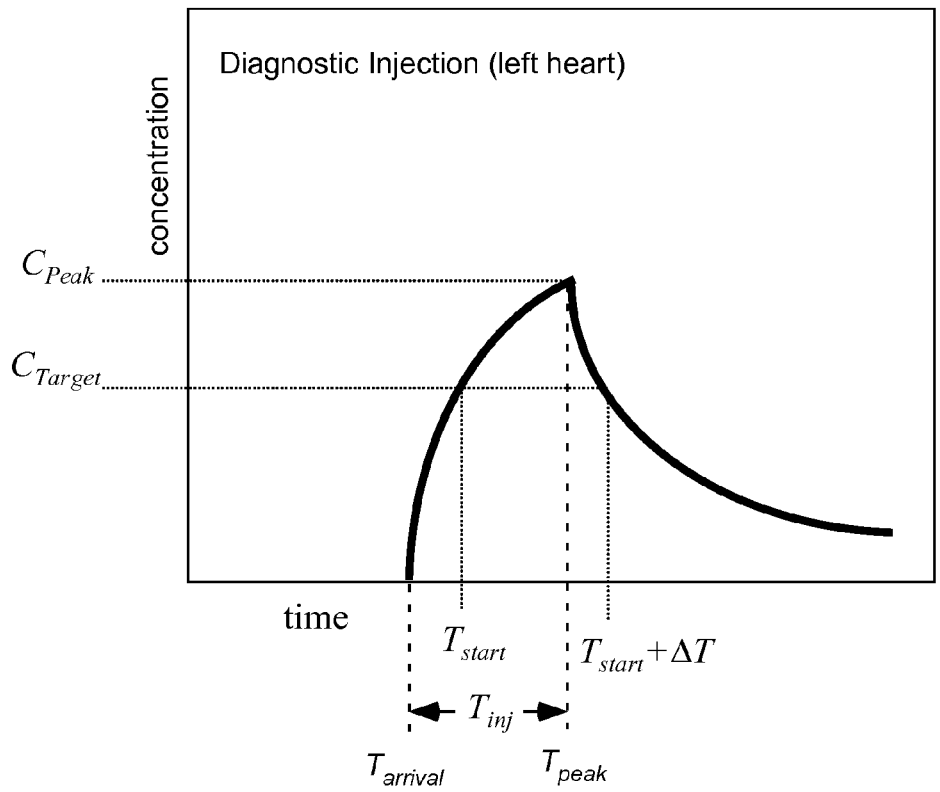
FIG. 4 is a sample concentration curves for a diagnostic injection, showing the peak and target concentrations in the scan window, wherein a scan start time $T_{start}$ and an injection duration $T_{inj}$ are relative to the arrival time of the contrast in the left heart.

For determining an appropriate flow rate and an appropriate injection duration for a given patient in several embodiments, blood concentrations of contrast enhancing agent can be modeled in the same way as in the estimation of cardiac output and blood volume. For example, two attributes are typically considered to be important to the generation of the diagnostic injection protocol: the peak concentration and the target concentration (defined as the concentration at the start and end of the scan window) of the left heart structures. As shown in FIG. 4, the concentration at peak enhancement $C_{Peak}$ for the left heart/ascending aorta (the second ROI in the representative studies of the present invention) occurs $T_{inj}$ seconds after the contrast arrives in the left heart. The scan begins at $T_{start}$, on an unknown point on the upslope of the left heart concentration curve. It ends $\Delta T$ seconds later at $T_{start}+\Delta T$ or $T_{end}$, where $\Delta T$ is the specified scan duration, on the downslope of the curve. To position the scan window in such a way that enhancement is both as high and as consistent as possible, those two values (on the upslope and downslope) can be set to be equal and are referred to as $C_{Target}$.

Given desired values for each of a desired peak concentration/enhancement and a desired target concentration/enhancement in one region of interest (for example, the aorta/left heart), and equally weighting the error in peak enhancement and the error in target enhancement in that region of interest, the following optimization can be used (wherein "Desired" values are provided/input by, for example, an operator):

$$Q_{inj}^*, T_{inj}^* = \underset{Q_{inj}, T_{inj}}{\operatorname{argmin}}\left(\left|DesiredPeak - C_{Peak}\right| + \left|DesiredTarget - C_{Target}\right|\right) \quad (8)$$

As clear to one skilled in the art, the arguments can be weighted other than equally in the above cost function and further arguments can be included. As also clear to one skilled in the art, additional or alternative optimizations can be performed.

To find $Q^*_{inj}$ and $T^*_{inj}$, the error function is defined in terms of $Q_{inj}$, $T_{inj}$, and known constants, using the analytical solution to the PK model. This is already true by definition for $C(T_{Peak})$ or $C_{Peak}$:

$$C_{Peak} = \frac{Q_{inj}}{Q_{CO}} C_i \left(1 - e^{-\frac{Q_{CO}}{V_B}T_{inj}}\right) \quad (9)$$

The value of $C(T_{start})$ or $C_{Target}$ on the upslope is also a function of $T_{start}$, the unknown time at which the scan begins.

$$C_{Target} = \frac{Q_{inj}}{Q_{CO}} C_i \left(1 - e^{-\frac{Q_{CO}}{V_B}T_{start}}\right) \quad (10)$$

On the downslope, $C_{Target}$ is the concentration at the end of the scan, which is a function of $C_{Peak}$ and $T_{start}$ (assuming the scan duration, $\Delta T$, is fixed).

$$C_{Target} = C_{Peak}\left(e^{\frac{-Q_{CO}}{V_B}(T_{start}+\Delta T - T_{inj})}\right) \quad (11)$$

Substituting in for $C_{Peak}$ and simplifying yields:

$$C_{Target} = \frac{Q_{inj}}{Q_{CO}}C_i\left(e^{\frac{-Q_{CO}}{V_B}(T_{start}+\Delta T - T_{inj})} - e^{\frac{-Q_{CO}}{V_B}(T_{start}+\Delta T)}\right) \quad (12)$$

At this point, there are two equations ($C_{Target}$ on the upslope and the downslope) and two unknowns ($C_{Target}$ and $T_{start}$). After solving algebraically for $C_{Target}$, the following expression in terms of only $Q_{inj}$, $T_{inj}$, and known constants is derived.

$$C_{Target} = \frac{\frac{Q_{inj}}{Q_{CO}}C_i\left(1 - e^{\frac{-Q_{CO}}{V_B}T_{inj}}\right)}{1 - e^{\frac{-Q_{CO}}{V_B}T_{inj}} + e^{\frac{-Q_{CO}}{V_B}(T_{inj}-\Delta T)}} \quad (13)$$

Figure 5:
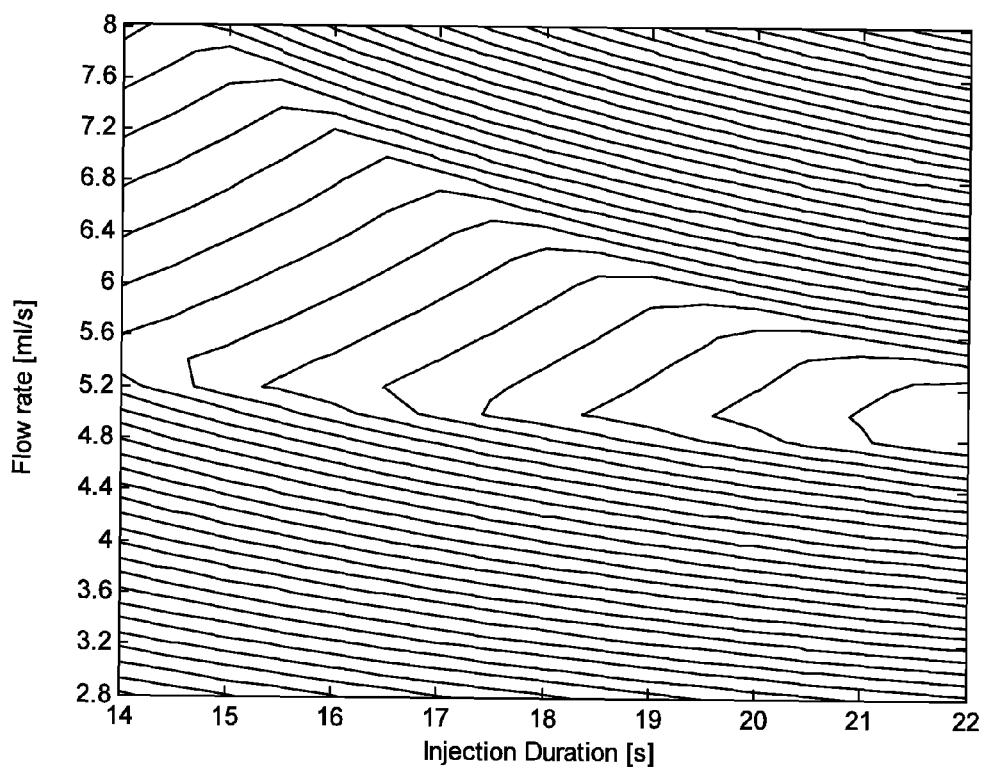
FIG. 5 illustrates a contour plot of the solution space for Equation (8) wherein $C_i$=370 mgI/ml, $C_{Peak}$=350 HU, $C_{Target}$=300 HU, $Q_{CO}$=6.1 L/min, and $V_B$=0.72 L.
Figure 6:
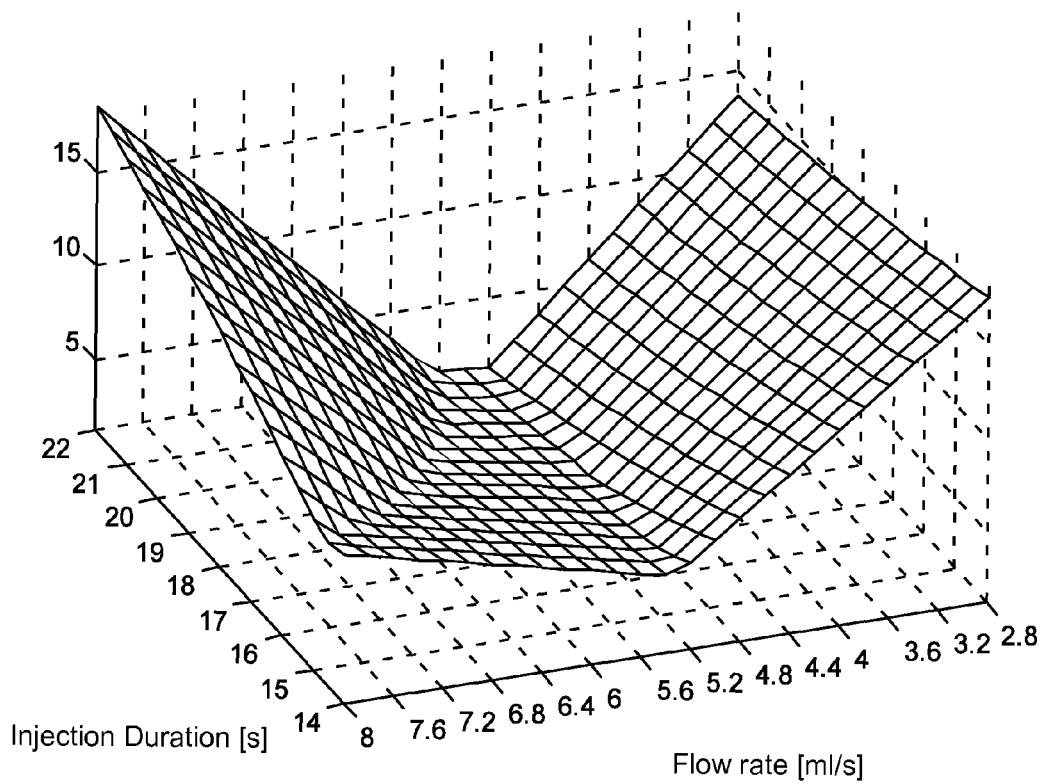
FIG. 6 illustrates a surface plot of the solution space for Equation (8) wherein $C_i$=370 mgI/ml, $C_{Peak}$=350 HU, $C_{Target}$=300 HU, $Q_{CO}$=6.1 L/min, and $V_B$=0.72 L.

Note that if $T_{inj} \gg \Delta T$, $C_{Target}$ approaches the numerator ($C_{Peak}$), and if delta $T \gg T_{inj}$, $C_{Target}$ goes to zero. Equations (9) and (13) are now substituted into equation (8) and the parameters that minimize the cost function are determined. There are several options for numerical solutions for $Q^*_{inj}$ and $T^*_{inj}$ including, but not limited to: a "brute force" search over a reasonable range/resolution of $Q_{inj}$ and $T_{inj}$; a relatively straightforward minimization such as Nelder-Mead (simplex); or a gradient descent (the partial derivatives can be computed analytically as well). In several studies, a brute force search strategy was implemented because the parameter range is well defined, the solution manifold is well behaved (as shown in the contour plot in FIG. 5 and surface plot in FIG. 6), and the computational burden needed to search for the minimum is insignificant, especially realizing that a computation time of several seconds in the interval between parameter entry and protocol generation has no impact on the procedure.

Injection Truncation and Dilution Phase Calculations

Once an initial, computed diagnostic protocol is generated (including the scan delay), a test is applied to ensure the contrast injection is terminated a given amount of time (for example, a few seconds) prior to the end of the scan. One obviously does not want to inject contrast media after the end of the scan because that contrast will not contribute to the diagnostic image. A more subtle consideration in optimal protocol generation arises in that, because of the transit delay from the injection site to the right heart (or other ROI), contrast injected within the time between the end of the scan and the transit time to, for example, the right heart also will not contribute to the diagnostic image. The minimum time needed for contrast to arrive in the right atrium was determined as the peak time of the pulmonary artery time enhancement curve minus the injection duration of the test bolus plus an offset factor in recognition that the contrast arrives in the right atrium before it transits to the pulmonary trunk. A default value of 2 seconds was used for the offset factor in several studies. As clear to those skilled in the art, the above considerations/logic apply to ROIs other than the left heart/right heart.

The scan delay can, for example, be computed by estimating a bolus arrival time using the formula:

$$\text{scanDelay} = T_2 - (T_{injTB} + \text{arrOffset}) + T_{start}$$

wherein $T_{injTB}$ is the injection duration of the timing bolus and arrOffset is an arrival time offset value; and a scan end time can be determined by adding the scan delay to the scan duration.

An arrival time of contrast in the right heart can, for example, be computed using the formula $$T_{arrRH} = T_1 - (T_{injTB} + \text{arrOffset})$$

wherein $T_{1Peak}$ is the time to peak enhancement in the first region of interest.

Figure 7A:
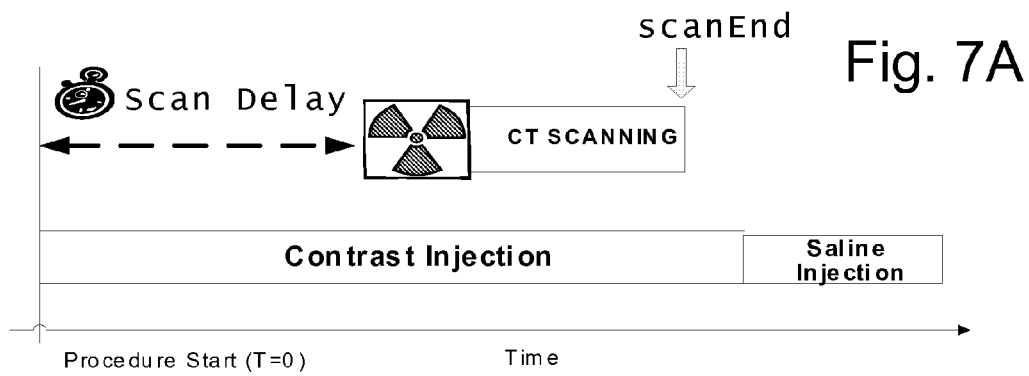
FIG. 7A illustrates an injection truncation scenario when the computed injection extends beyond the end of the scan.
Figure 7B:
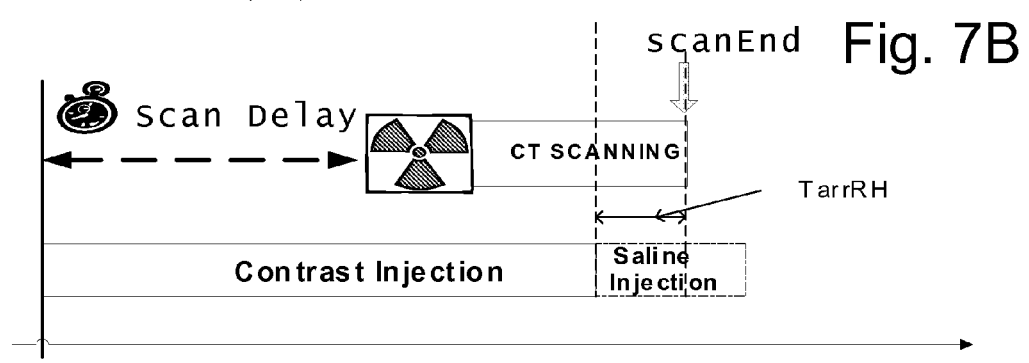
FIG. 7B illustrates the truncated protocol resulting from the truncation scenario of FIG. 7A.
Figure 8A:
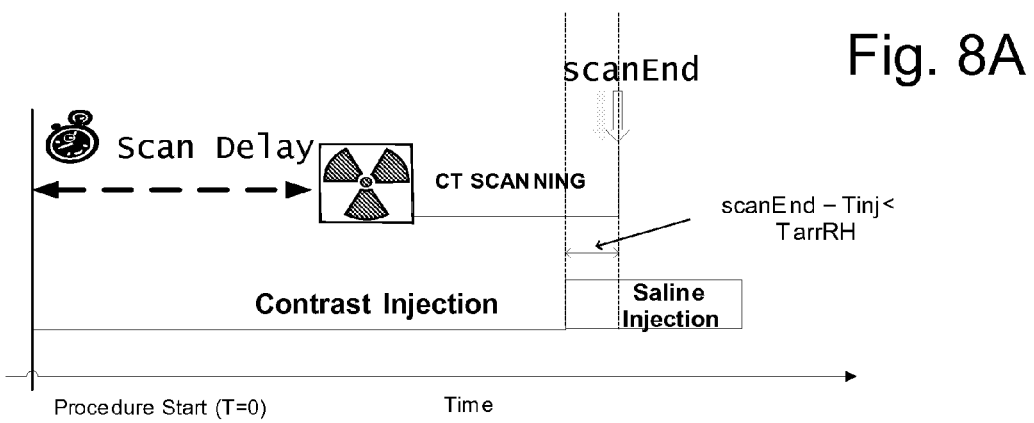
FIG. 8A illustrates a protocol truncation scenario in which the computed injection duration terminates without enough time for the final volume of contrast to arrive in the territory of interest before the scan ends.
Figure 8B:
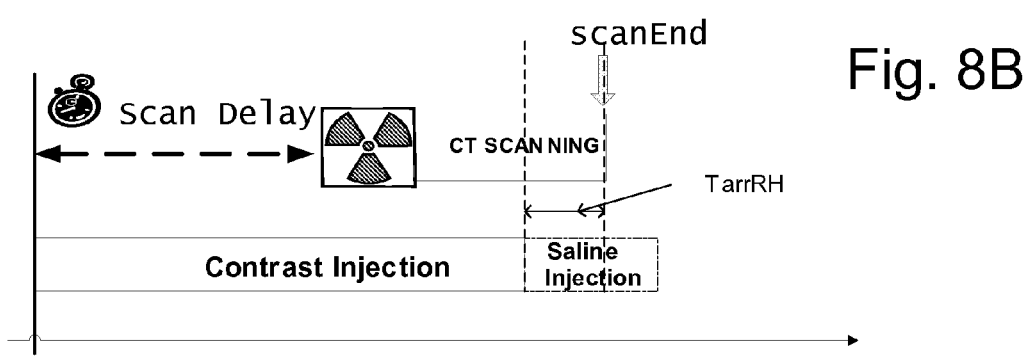
FIG. 8B illustrates the "fixed" protocol resulting from the protocol truncation scenario of FIG. 8A.

FIG. 7A depicts a scenario in which the computed diagnostic injection extends beyond the end of the scan. FIG. 7B depicts a resulting diagnostic injection after a truncation algorithm or methodology of the present invention is executed. After the truncation, the injection is finished a few seconds prior to the end of the scan (defined by the arrival time of the contrast to the right heart) ensuring that unneeded contrast is not injected into the patient. Because the protocol generation in this algorithm is data driven, it is not anticipated that the truncation operation described above will occur too frequently. In that regard, the duration of the injection is fitted via an optimization methodology using timing data generated from the test bolus. A more common scenario, however, is depicted in FIG. 8A. In this scenario, the computed diagnostic injection ends prior to the completion of the scan. However, the contrast injected in the last few seconds of the injection will not have enough time to migrate into the right heart (as determined by the arrival time of contrast to the right heart measured from the pulmonary trunk time enhancement curve) and will not contribute to the diagnostic image. Therefore the injection is clamped/stopped at the difference between the end of the scan and the arrival of contrast in the right heart. The resulting injection protocol is presented in FIG. 8B.

In that regard, the injection can be truncated if ($T_{inj} + T_{arrRH}$)>scanEnd. The injection can, for example, be truncated so that it is finished at least $T_{arrRH}$ seconds before end of the scan as follows:

$$T_{inj} = \text{scanEnd} - T_{arrRH}.$$

After the contrast injection protocol is checked and modified, if necessary, to prevent extension beyond the end of the scan and that contrast is not unnecessarily injected, a dual-flow (or dilution) phase, in which both contrast and a diluent are injected simultaneously, can be computed. The approach of the present invention is different than previous embodiments in that every protocol does not necessarily have a dual-flow protocol. The dilution phase is, for example, designed to reduce bright opacification of the superior vena cava (SVC) and right heart structures, which may result in streak and beam hardening artifacts.

Figure 9A:
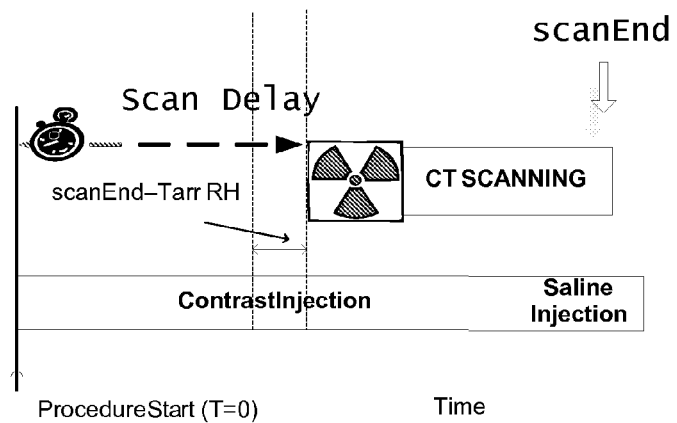
FIG. 9A illustrates one embodiment of a manner in which a dual-flow (dilution) phase is computed, wherein an objective is to have diluted contrast arriving in the territory of interest as the scan starts; and wherein undiluted contrast will be flooding the right heart as the scan starts.
Figure 9B:
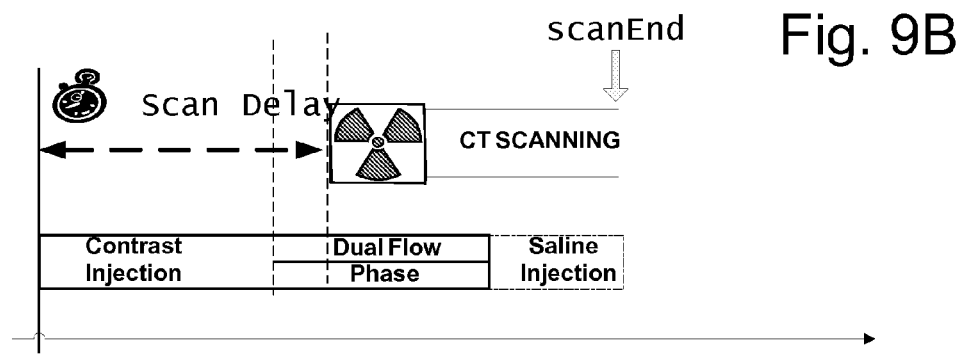
FIG. 9B illustrates the protocol generated using the dual-flow computation of FIG. 9A.

In several embodiments, a comparison of the scan start and the injection is made to determine when a dilution phase should be inserted. If the scan starts while the contrast injection is proceeding, it is reasoned that diluted contrast should be "cut in", or started, N seconds prior to the start of the scan because the diluted contrast will be filling the right heart structures as the scan starts (where N is the arrival of contrast to the right heart). If the contrast dilution does not start within the time frame between the start of the scan minus the bolus arrival time into the right heart, than undiluted contrast will be filling the SVC etc., increasing the chance of streak and over opacification. A pictorial description of the dilution phase computation is provided in FIG. 9A. The resulting injection protocol with a DualFlow phase is given in FIG. 9B. As described above, the ratio of contrast/saline was fixed or dependent on scan/subject parameters to be 40/60 (contrast/saline) in several studied to reduce the degrees of freedom in the experiment. As clear to one skilled in the art, contrast/saline ratios can readily be generated that are variable (for example, as described in PCT International Patent Application No. PCT/US2007/026194 or as further described below). For example, a ratio of contrast enhancing fluid to non-contrast enhancing fluid in an admixture or dual-flow phase can be determined on the basis of time to peak enhancement determined during the test bolus. A longer time to peak enhancement can, for example, result in a higher ratio of contrast enhancing fluid to non-contrast enhancing fluid.

Figure 10A:
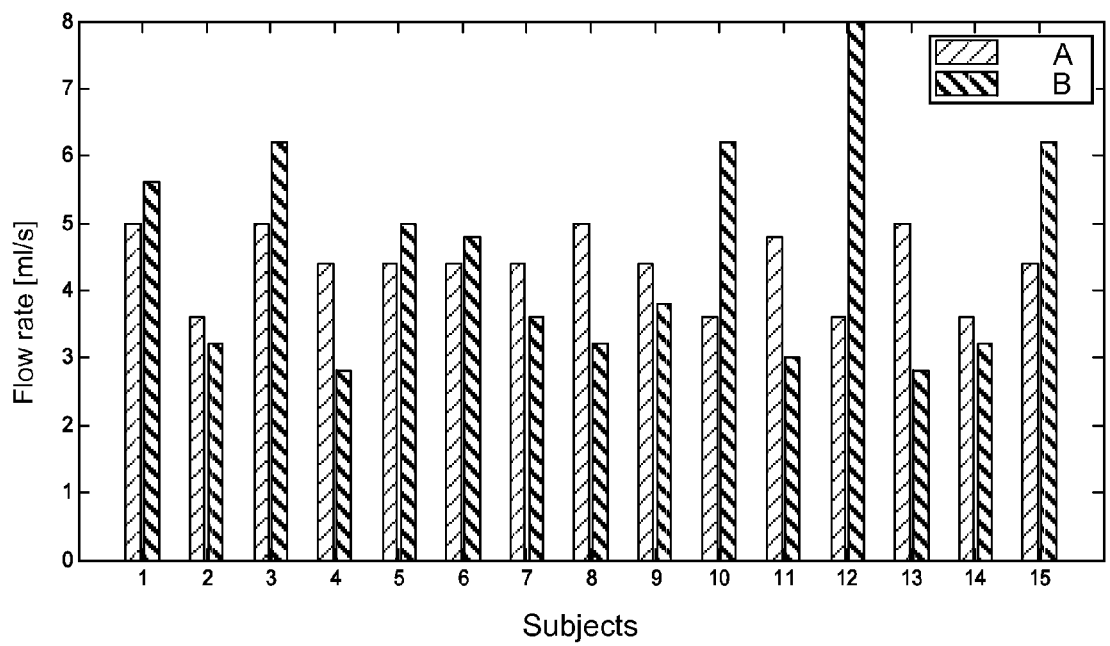
FIG. 10A illustrates a comparison over 15 sample subjects of flow rates determined using a methodology (A) set forth in PCT International Patent Application No. PCT/US2007/026194 and a first embodiment of a methodology (B) of the present invention.

The protocol generation algorithms described above can, for example, be used to minimize the dose of contrast a subject receives by considering that subject's cardiac dynamics, drug properties and scan properties. FIG. 10A sets forth flow rates calculated using the methodology of the present invention (B) as compared to the rates calculated using the methodology set forth in PCT International Patent Application No. PCT/US2007/026194 (A). The flow rates determined using the methodology of the present invention are similar in magnitude to those calculated using the other methodology, yet show a greater variability, which one would expect because the methodology of the present invention attempts to generate more patient specific injection protocols with variable flow rates. The comparison is made as a check of the algorithms clinical validity. For example, if a majority of resulting flow rate values were calculated to be greater than 10 ml/s or less than 3 ml/s, this might indicate a flaw in the algorithmic logic.

FIG. 10B illustrates data obtained in a study group of 70 patients scheduled for clinically indicated dual source CT or DSCT studies using methodology 1 as described above. In the studies of the study group, contrast having a concentration of 300 mgI/ml was injected. A targeted attenuation level of 250 HU was used. ECG pulsing was also used to minimize radiation dosing. In the data, Asc.Aorta refers to Ascending Aorta, Left_Main refers to the Coronary Artery, LAD_Proximal refers to the Proximal Region of the Left Anterior Descending Coronary Artery, LAD_Middle refers to the Middle Region of the Left Anterior Descending Coronary Artery, LAD_Distal refers to the Distal Region of the Left Anterior Descending Coronary Artery, LCX_Proximal refers to the Proximal Region of the Left Circumflex Artery, LCX_Middle refers to the Middle Region of the Left Circumflex Artery, LCX_Distal refers to the Distal Region of the Left Circumflex Artery, RCA_Proximal refers to the Proximal region of the Right Coronary Artery, RCA_Middle refers to the Middle region of the Right Coronary Artery, and RCA_Distal refers to the Distal region of the RCA.

A control group of 50 patients scheduled for clinically indicated dual source CT or DSCT studies was also studied. In the studies of the control group, contrast having a concentration of 300 mgI/ml was injected. A routine triphasic injection protocol was used with the control group. In the triphasic injection protocol, 60-90 ml of contrast medium was first injected, followed by a dual flow injection of 50 ml of fluid having a contrast medium/saline ration of 30/70, followed by injection of saline. The flow rate for each phase was 6 ml/sec.

Figure 10C:
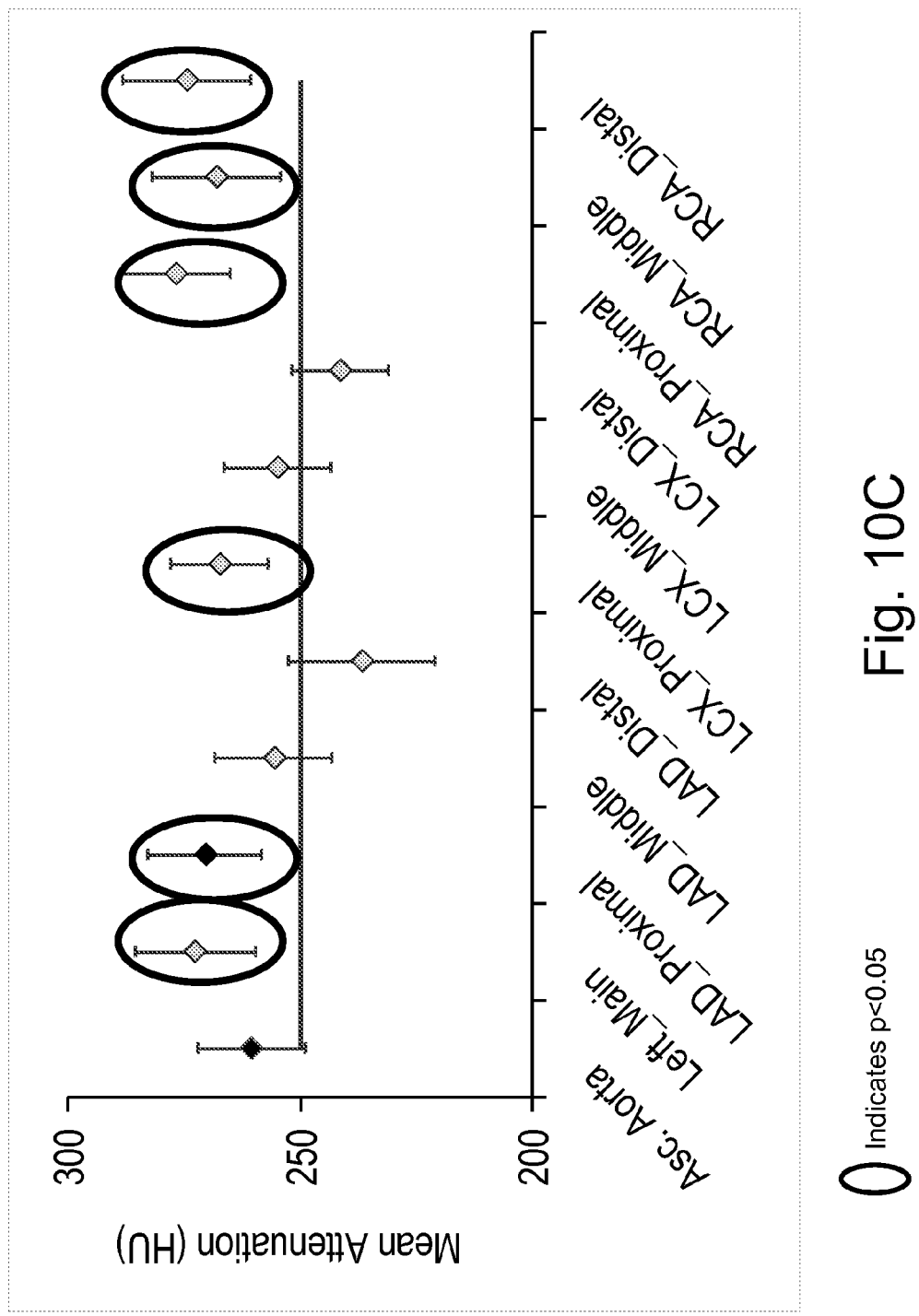
FIG. 10C illustrates mean attenuation (HU) for each of the anatomy regions studied for the study group of FIG. 10B.
Figure 10D:
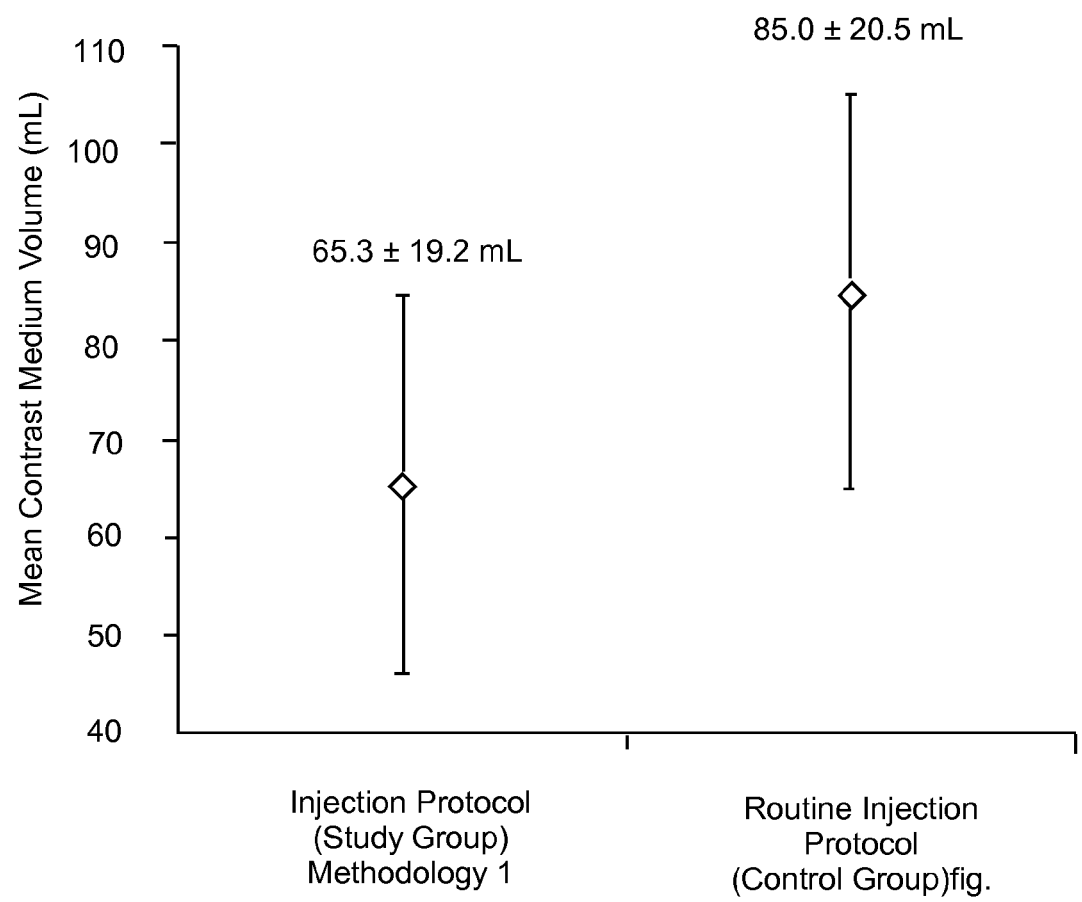
FIG. 10D illustrates mean contrast medium volume used in the studies of each of the study group and a control group.
Figure 10E:
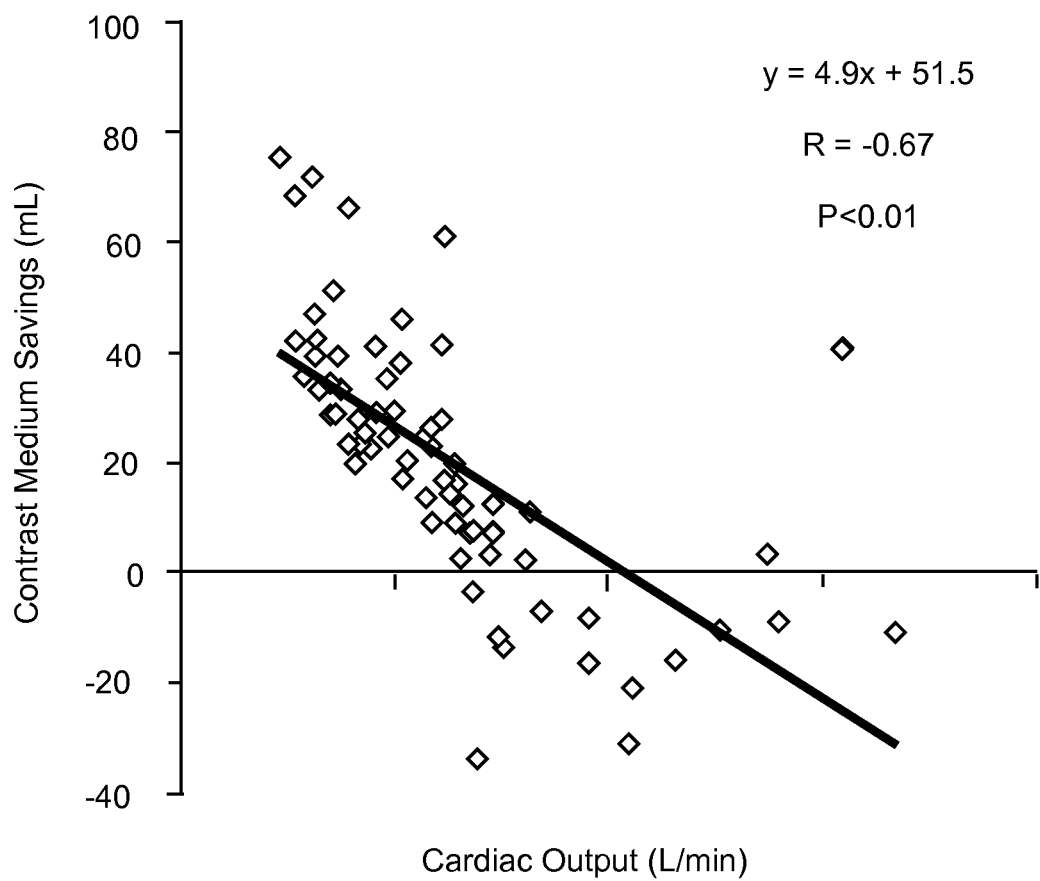
FIG. 10E illustrates a graph of contrast medium savings (mL) as a function of cardiac output.

FIG. 10C illustrates mean attenuation (HU) for each of the anatomy regions studied for the study group. FIG. 10D illustrates mean contrast enhancement fluid or contrast medium volume used in the studies of each of the study group and the control group. A mean savings of approximately 19.7±24.1 mL of contrast per patient was achieved using the methodology of the present invention. FIG. 10E illustrates a graph of contrast medium savings (mL) as a function of cardiac output. As illustrated the systems and methods of the present invention provide contrast medium savings over a wide range of contrast medium. There are cases for subjects with high cardiac output that the algorithm computes a protocol that requires more contrast than would otherwise be delivered. In those cases, it is possible that the standard control protocol would provide insufficient enhancement (<250 HU). FIG. 10F illustrates mean attenuation for the control group and the study group for each of the regions studied. For the study group, there is less variability across regions (it is more consistently close to 250 HU) as compared to the control, which has inconsistent enhancement patterns (note the higher enhancement in the Asc Aorta and the lower enhancement in the distal regions).

A summary of the workflow of the above-identified embodiment of a methodology of the present invention as applied in connection with the pulmonary artery and ascending aorta is set forth below:

1: Get Patient and Procedure information:
   a. Get contrast concentration: $C_i$
   b. Get the maximum flow rate allowable: $Q_{MAX}$
   c. Get scan duration from user: $\Delta T$
   d. Get Hounsfield to plasma concentration conversion factor HutoMgI for the scanner (default=25 HU/(mgI/ml))
   e. Get desired peak enhancement DesiredPeak and desired target enhancement at start and stop of scan window DesiredTarget
   f. Generate a test bolus injection protocol, default Q is 5 ml/s and volume=20 ml (4 second $T_{inj}$), saline flush phase, Q=5 ml/s, vol=40 ml
2: From test bolus, get times to peak for the pulmonary artery enhancement curve and the ascending aorta enhancement curve from user: $T_1$ and $T_2$
3: Get peak enhancement values from the pulmonary artery and the ascending aorta bolus enhancement curves, and convert to concentration units using HutoMgI $C_{1PA}$ and $C_{2AO}$
4: Estimate Cardiac Output and Blood Volume Subroutine
   a. Compute Cardiac Output estimate ($Q_{CO}$) using Equation 7
   b. Compute Blood Volume estimate ($V_B$) using Equation 6
5: Estimate Diagnostic Protocol Subroutine
   a. Compute peak ($C_{Peak}$) and target ($C_{Target}$) enhancements in 1 the aorta using Equations (9) and (13), respectively, for all admissible input values for $T_{inj}$ and $Q_{inj}$
     i. Maximum $Q_{inj}$=maxFlowRate
     ii. Minimum $Q_{inj}$=3.5 ml/s for 300 mgI/ml contrast, 2.8 ml/s for 370 mgI/ml contrast (Iodine administration rate of 1 gI/s per Rist et al)
     iii. Maximim $T_{inj}$=$\Delta T$+8
     iv. Minimum $T_{inj}$=$\Delta T$
   b. Find values for the diagnostic protocol flow rate $Q^*_{inj}$ and injection duration $T^*_{inj}$ which are the arguments that minimize the cost function in Equation 8:
6: Compute Injection Protocol Subroutine—Including Dilution Phase
   a. Compute the total diagnostic phase contrast volume: $Vol_{tot}=Q_{inj}*T_{inj}$
   b. Define an arrival time offset value: arrOffset=2 seconds c. Compute the scan delay by estimating the bolus arrival time, where $T_2$ is the time to the second peak: scanDelay=$T_2$-($T_{injTB}$+arrOffset)+$T_{start}$ d. Compute the end point of the scan: scanEnd=scanDelay+$\Delta T$ e. Compute the arrival time of the contrast in the right heart, where $T_1$ is the time to the first peak: $T_{arrRH}$=$T_1$-($T_{injTB}$+arrOffset)

f. Use the computed $T_{arrRH}$, scanEnd, and $T_{inj}$ to determine if/when the injection should be truncated.
   i. if ($T_{inj}$+$T_{arrRH}$)>scanEnd
   ii. then we truncate the injection protocol so that it is finished at least TarrRH seconds before end of the scan: $T_{inj}$=scanEnd-$T_{arrRH}$ g. Use the computed $T_{arrRH}$, scanDelay, and $T_{inj}$ to determine if/when a dilution DualFlow phase should be initiated.
   i. if ($T_{inj}$+$T_{arrRH}$)>scanDelay
   ii. then we "cut over" to the DualFlow phase so that diluted contrast is entering the right heart during the scan: $T_{startDF}$=scanDelay-$T_{arrRH}$ h. Define DualFlow ratio: $DF_{ratio}$=0.40 i. Determine the duration of the DualFlow phase:
   i. $T_{endDF}$=$T_{inj}$
   ii. $DF_{dur}$=$T_{endDF}$-$T_{startDF}$ j. Compute volumes for three phases of injection:
   i. $Vol_{DF}$=$DF_{dur}$*$Q_{inj}$
   ii. $Vol_{Contrast}$=$Vol_{tot}$-$Vol_{DF}$;
   iii. $Vol_{Saline}$=40

In the above studies, an injection flow rate was calculated. It is also possible, for example, to vary the iodine administration rate during the diagnostic injection instead of the flow rate. The resulting enhancement geometry may be slightly different. In one embodiment, the volumetric flow rate is fixed for all patient, but the Iodine Administration Rate (gI/s) is adjusted by diluting the contrast during the diagnostic injection, if required. Only if the stock concentration cannot provide sufficient enhancement, would the volumetric flow rate be increased.

In the embodiments described above, the scan begins at $T_{start}$, on an unknown point on the upslope of the left heart concentration curve. The scan ends $\Delta T$ seconds later (where $\Delta T$ is the specified scan duration) on the downslope of the curve. To time the scan window in a manner to achieve relatively high and consistent enhancement, those two values (referred to as $C_{LH-Start}$ on the upslope and $C_{LH-End}$ on the downslope) should be as close to $C_{LH-Target}$ as possible. The right heart curve has similar associated parameters. However, because $C_{RH-Peak}$ should not occur during the scan window (as too much enhancement in the right heart could lead to streaking or beam hardening artifacts), it was not included as a term in the cost function set forth in Equation (8).

Diagnostic Injection Protocol Generation with Variable Dilution Ratio and Optimization for Concentration/Enhancement in an Additional Region of Interest—Methodology 2

Figure 11:
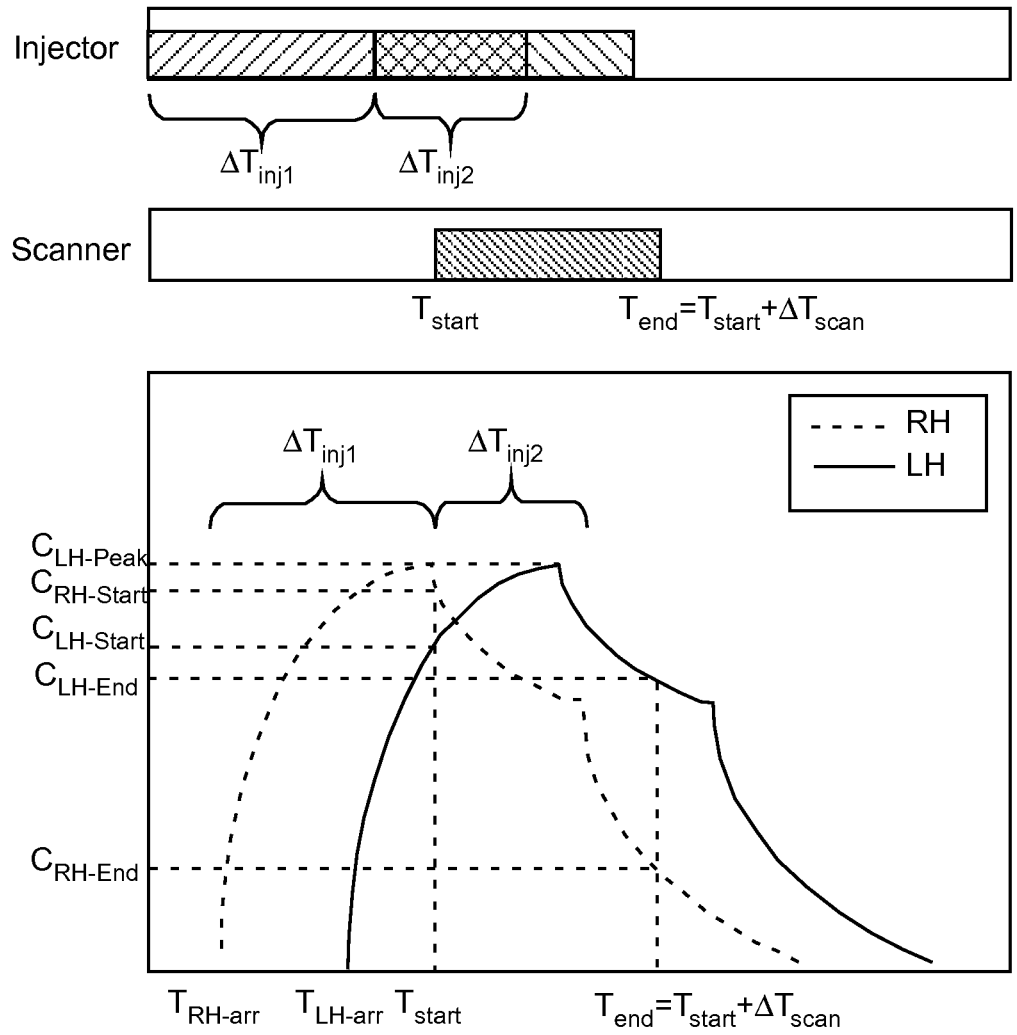
FIG. 11 illustrates an example of relative timing and diagnostic injection protocol phases, scan and enhancement curves.

In another embodiment of a protocol generation system and method of the present invention, parameters are added in the optimization procedure related to the dilution phase. For example, the dilution ratio ($R_2$) and the duration of the dilution phase ($\Delta T_{inj2}$) can be added to the optimization procedure. The dilution ratio is thereby personalized (instead of using a fixed or set ratio of, for example, 40/60). Further, there is no need to adjust the computed protocol after optimization Enhancement targets are also added to the optimization procedure (for example, cost function) for a second region of interest (the right heart or RH in the representative examples herein) in this embodiment. Because the best placement of the scan window does not depends solely on left heart or LH enhancement in the representative examples of this embodiment set forth herein, there is no analytic expression for $T_{start}$. $T_{start}$ is thus also included as a parameter in the optimization procedure. FIG. 11 illustrates an example of relative timing and diagnostic injection protocol phases, scan and enhancement curves for the right heart/pulmonary artery and left heart/aorta.

Another term was added to cost function as a penalty on the total volume of contrast injected (see the last term of the cost function of Equation (14)). Weighting factors such as $\alpha$, $\beta$, and $\gamma$ in Equation (14) were included to allow for adjustment of the relative importance of the terms of the cost function. For example, by using a small value for $\alpha$, error in right heart enhancement is penalized less heavily than error in left heart enhancement. Because the scan window is not centered on the right heart peak, it is typical that $C(T_{RH-Start})$ or $C_{RH-Start}$ will be too high and $C(T_{RH-End})$ or $C_{RH-End}$ will be too low. Therefore, to avoid having the optimization dominated by such errors in right heart enhancement, set $\alpha$ was set to equal 0.5 in several embodiments. $\beta$ was set to equal 1 in several embodiments, which was shown to be a reasonable trade-off between losing consistency with the test bolus flow rate and not reaching target enhancement levels. In several embodiments $\gamma$ was set to equal 1000, which puts a very large penalty on exceeding the loaded contrast volume. In that regard, if $(Q_{inj}(R_1\Delta T_{inj1}+R_2\Delta T_{inj2})>V_{Load})$ was true, $\gamma$ was set to equal 1000. Otherwise, $\gamma$ was set to equal 0.

$$T^*_{start}, Q^*_{inj}, R^*_1, \Delta T^*_{inj1}, R^*_2, \Delta T^*_{inj2} = \underset{\substack{T_{start}, Q_{inj}, \\ R_1, \Delta T_{inj1}, \\ R_2, \Delta T_{inj2}}}{\arg\min} \begin{pmatrix} |C_{LH-Peak} - C_{LH-Peak-Desired}| + \\ |C_{LH-Start} - C_{LH-Target-Desired}| + \\ |C_{LH-End} - C_{LH-Target-Desired}| + \\ \alpha|C_{RH-Start} - C_{RH-Target-Desired}| + \\ \alpha|C_{RH-End} - C_{RH-Target-Desired}| + \\ \beta|Q_{inj} - Q_{TB}| + \\ \gamma, \text{if}(Q_{inj}(R_1\Delta T_{inj1} + R_2\Delta T_{inj2}) > V_{Load}) \end{pmatrix} \quad (14)$$

Depending on the dilution ratios, the peak value for the LH occurs during the upslope (phase 1) or dilution phase (phase 2), and is therefore the greater of the two:

$$C_{LH-Peak} = \frac{Q_{inj}}{Q_{CO}} C_i R_1 \left(1 - e^{-\frac{Q_{CO}}{V_B}\Delta T_{inj1}}\right) \quad (15)$$

or $$C_{LH-Peak} = \frac{Q_{inj}}{Q_{CO}} C_i R_1 \left(1 - e^{-\frac{Q_{CO}}{V_B}\Delta T_{inj1}}\right) e^{-\frac{Q_{CO}}{V_B}\Delta T_{inj2}} + \frac{Q_{inj}}{Q_{CO}} C_i R_2 \left(1 - e^{-\frac{Q_{CO}}{V_B}\Delta T_{inj2}}\right) \quad (16)$$

For the remaining concentration values, given an absolute time T (either the start or end of the scan), the RH and LH curves can each be in one of 3 regions—upslope (phase 1), dilution (phase 2), or decay (phase 3). When $T<(T_{arr}+\Delta T_{inj1})$, the expression is:

$$C_T = \frac{Q_{inj}}{Q_{CO}} C_i R_1 \left(1 - e^{\frac{-Q_{CO}}{V_B}(T - T_{arr})}\right) \quad (17)$$

Note that $T_{arr}$ is either $T_{RH-arr}$ or $T_{LH-arr}$, depending on which curve is being used. For the dilution phase (phase 2), when $(T_{arr} + \Delta T_{inj1}) < T < (T_{arr} + \Delta T_{inj1} + \Delta T_{inj2})$, the expression is:

$$C_T = \frac{Q_{inj}}{Q_{CO}} C_i R_1 \left(1 - e^{\frac{-Q_{CO}}{V_B} \Delta T_{inj1}}\right) e^{\frac{-Q_{CO}}{V_B}(T - (T_{arr} + \Delta T_{inj1}))} + \quad (18)$$

$$\frac{Q_{inj}}{Q_{CO}} C_i R_2 \left(1 - e^{\frac{-Q_{CO}}{V_B}(T - (T_{arr} + \Delta T_{inj1}))}\right)$$

Finally, in the decay phase (phase 3), when $T > (T_{arr} + \Delta T_{injA} + \Delta T_{injAB})$, the expression is:

$$C_T = \left( \begin{array}{c} \frac{Q_{inj}}{Q_{CO}} C_i R_1 \left(1 - e^{\frac{-Q_{CO}}{V_B} \Delta T_{inj1}}\right) e^{\frac{-Q_{CO}}{V_B} \Delta T_{inj2}} + \\ \frac{Q_{inj}}{Q_{CO}} C_i R_2 \left(1 - e^{\frac{-Q_{CO}}{V_B} \Delta T_{inj2}}\right) \end{array} \right) \quad (19)$$

$$e^{\frac{-Q_{CO}}{V_B}(T - (T_{arr} + \Delta T_{inj1} + \Delta T_{inj2}))}$$

Therefore, to find a given concentration on a given curve at a given time, one specifies the arrival time corresponding to the curve (RH or LH), determines which phase is occurring at time T, and uses the appropriate equation as set forth above.

Although the search space grew from a two-dimensional search space in Equation (8) to six-dimensional search space in Equation (14), a brute force search strategy was still implemented. The parameter range is well defined, the solution manifold is well behaved and the computational burden needed to search for the minimum is still not significant in the case of a relatively coarsely sampled grid (for example, flow rates at 0.1 ml/s, dilution ratios at 10%, and times at 1 second). Further, a computation time of several seconds in the interval between parameter entry and protocol generation has no impact on the imaging procedure.

Figure 12:
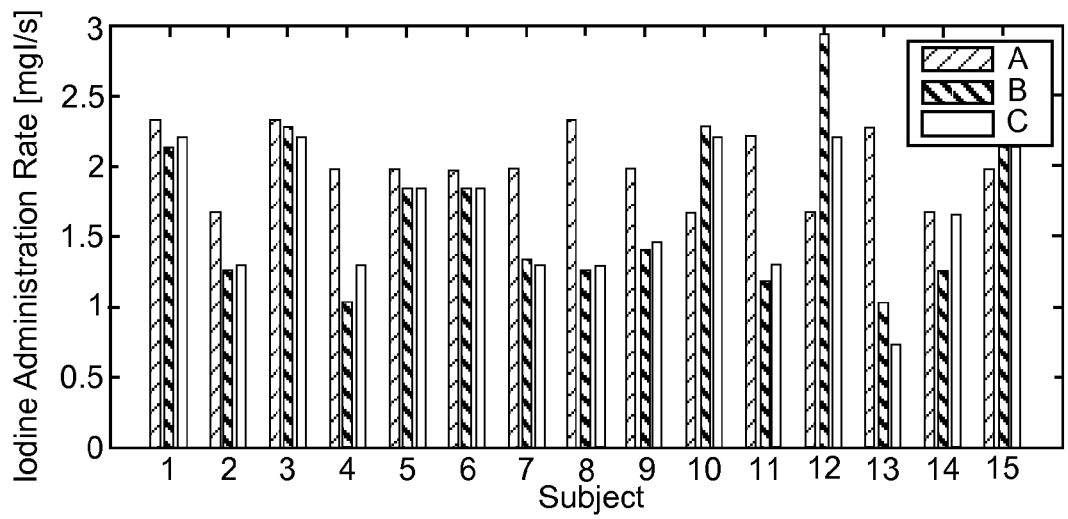
FIG. 12 illustrates a comparison of iodine administration rate over 15 sample subjects as determined using the methodology (A) as set forth in PCT International Patent Application No. PCT/US2007/026194, using a first embodiment of a methodology (B) of the present invention in which a dilution ratio for a dilution phase is fixed and right heart enhancement factors/arguments are not included in an optimization cost function, and using a second embodiment of a methodology (C) of the present invention in which a dilution ratio for a dilution phase varies and right heart enhancement factors/arguments are included in an optimization cost function.
Figure 13:
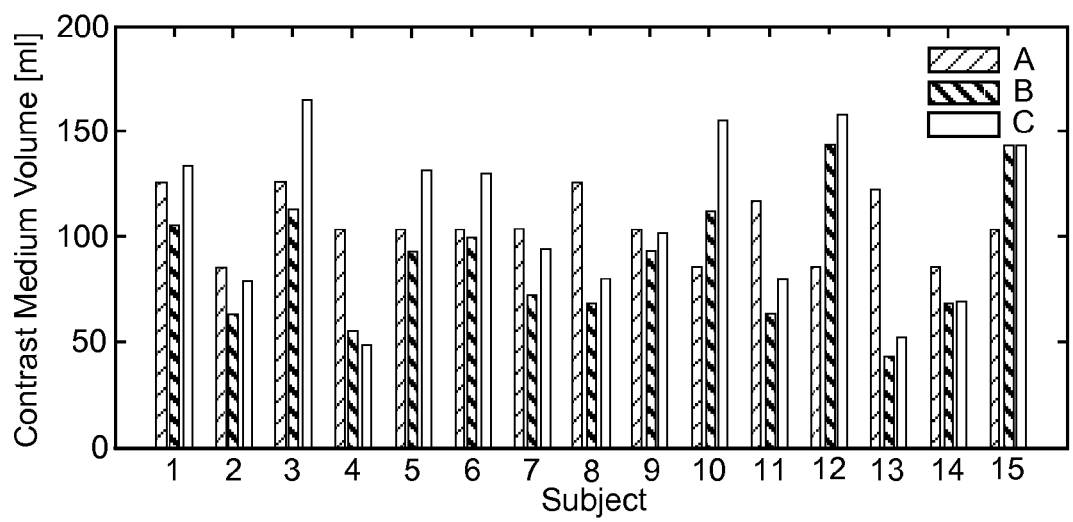
FIG. 13 illustrates a comparison of contrast medium volume (CM volume) rate over 15 sample subjects as determined using the methodology (A) as set forth in PCT International Patent Application No. PCT/US2007/026194, using a first embodiment of a methodology (B) of the present invention in which a dilution ratio for a dilution phase is fixed and right heart enhancement factors/arguments are not included in an optimization cost function, and using a second embodiment of a methodology (C) of the present invention in which a dilution ratio for a dilution phase varies and right heart enhancement factors/arguments are included in an optimization cost function.

Similar to the previous embodiment, the protocol generation procedure described above can be used to minimize the dose of contrast a subject receives considering the subject's cardiac dynamics, the drug properties and the scan properties. FIGS. 12 and 13, respectively, present iodine administration rates and total contrast volumes using the optimization procedure of Equation (14) (C) as compared to the methodology set forth in PCT International Patent Application No. PCT/US2007/026194 (A), and the methodology encompassing the optimization procedure of Equation (14) (B). The comparison provides a check of clinical validity.

Figure 14:
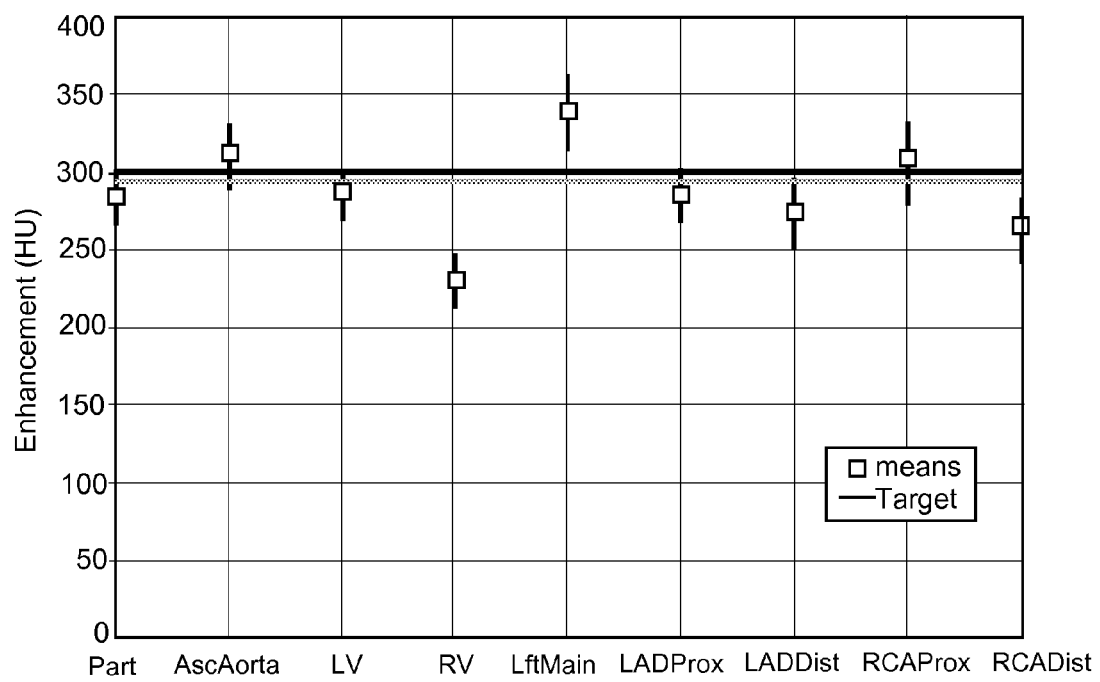
FIG. 14 illustrates clinical data collected from ten subjects undergoing DSCT cardiac imaging (Siemens Definition) under a second embodiment of the present invention.
Figure 15:
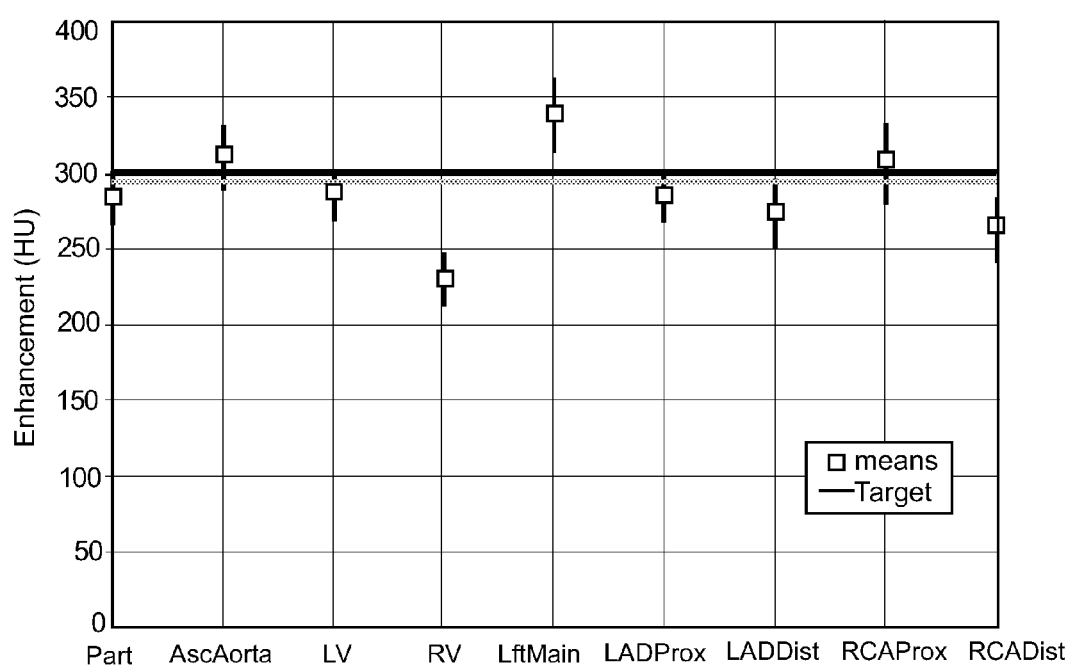

FIG. 14 illustrates clinical data collected from ten subjects undergoing DSCT cardiac imaging (Siemens Definition) under methodology 2 as described above. Mean values set forth in FIG. 14 are the mean of three regions of interests placed in each of the anatomical regions. The target enhancement for all anatomical regions (except for the pulmonary artery trunk and the right ventricle) was 300 HU. The error bars illustrated are ±1 standard deviation. The anatomical regions studied were Part (Pulmonary Artery Trunk), AscAorta (Ascending Aorta), RV (Right Ventricle), LftMain (Left Main Coronary Artery), LAD Prox (Proximal Region of the Left Anterior Descending Coronary Artery), LAD Dist (Distal region of the LAD coronary artery), RCA Prox (Proximal region of the Right Coronary Artery), RCA Dist (Distal region of the RCA).

A summary of the workflow of the above-identified embodiment of a methodology of the present invention (methodology 2) as applied in connection with the pulmonary artery and ascending aorta is set forth below:

1: Get Patient and Procedure information:
  a. Get contrast concentration: $C_i$
  b. Get the maximum flow rate allowable: $Q_{MAX}$
  c. Get scan duration from user: $\Delta T$
  d. Get Hounsfield to plasma concentration conversion factor HutoMgI for the scanner (default=25 HU/(mgI/ml))
  e. Get desired LH enhancement at start and stop of scan window LHTarget and desired RH enhancement at start and stop of scan window RHTarget
  f. Generate a test bolus injection protocol, default Q is 5 ml/s and volume=20 ml (4 second $T_{inj}$), at a 50/50 contrast ratio, followed by saline flush phase, Q=5 ml/s, vol=40 ml
2: From test bolus, get times to peak for the pulmonary artery enhancement curve and the ascending aorta enhancement curve from user: $T_1$ and $T_2$
3: Get peak enhancement values from the pulmonary artery and the ascending aorta bolus enhancement curves, and convert to concentration units using HutoMgI: $C_{1PA}$ and $C_{2AO}$
4: Estimate Cardiac Output and Blood Volume Subroutine
  a. Compute Cardiac Output estimate ($Q_{CO}$) using Equation (7).
  b. Compute Blood Volume estimate ($V_B$) using Equation (6)
5: Estimate Diagnostic Protocol Subroutine
  a. Compute peak $C_{LH\_Peak}$, $C_{LH\_start}$, $C_{LH\_end}$, $C_{RH\_start}$, and $C_{RH\_end}$ enhancements using Equations 9, 10, 11, 12 and 13, respectively, for all admissible input values for $T_{start}$, $Q_{inj}$, $R_1$, $\Delta T_{inj1}$, $R_2$, $\Delta T_{inj2}$.
    i. $T_{start}$ range=$T_{LH-arr}$ to 30
    ii. $Q_{inj}$ range=$Q_{injTB}$ to $\min(Q_{injTB}+1, Q_{MAX})$
    iii. $R_1$ range=0.1 to 1.0
    iv. $\Delta T_{inj1}$ range=$\Delta T_{scan}$ to $\Delta T_{scan}+8$
    v. $R_2$ range=0.05 to 0.95
    vi. $\Delta T_{inj2}$ range=0 to $\Delta T_{scan}$
  b. Find values for $T^*_{start}$, $Q^*_{inj1}$, $R^*_1$, $\Delta T^*_{inj1}$, $R^*_2$, $\Delta T^*_{inj2}$, which are the arguments that minimize the cost function of Equation 14.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method of determining at least one parameter for an injection procedure to be performed in combination with an imaging procedure, the method comprising the steps of:
  (a) injecting a test bolus of a contrast enhancement fluid having a contrast enhancing agent therein;
  (b) scanning at least two regions of interest with an imaging system as the test bolus of the contrast enhancement fluid flows therethrough to obtain therefrom a contrast time enhancement curve for each of the at least two regions of interest;

(c) extracting at least one discrete data point from each of the contrast time enhancement curves such that each of the discrete data points constitutes a pair of measurements on the contrast time enhancement curve corresponding thereto;

(d) substituting into a model the discrete data points extracted from the contrast time enhancement curves to obtain therefrom at least an estimate of values of physiological variables; and (e) using the at least an estimate of the values of the physiological variables to determine via the model the at least one parameter for the injection procedure to be performed in combination with the imaging procedure.

2. The method of claim 1 wherein the physiological variables are related to cardiopulmonary function.

3. The method of claim 2 wherein the at least one parameter is a parameter of at least one phase of the injection procedure for the injection of the contrast enhancement fluid or a parameter of the imaging system.

4. The method of claim 2 wherein the discrete data point(s) from the contrast time enhancement curve of a first of the regions of interest corresponds to a first pass of the contrast enhancement fluid through the first region of interest, and the discrete data point(s) from the contrast time enhancement curve of a second of the regions of interest corresponds to a first pass of the contrast enhancement fluid through the second region of interest.

5. The method of claim 4 wherein an analyzed portion of the contrast time enhancement curve of the first region of interest overlaps an analyzed portion of the contrast time enhancement curve of the second region of interest in time.

6. The method of claim 4 wherein a contrast enhancing agent concentration on one of the contrast time enhancement curves at a certain time is related to a contrast enhancing agent concentration on the other of the contrast time enhancement curves at the certain time or a time in proximity to the certain time using a conservation of mass balance.

7. The method of claim 6 wherein it is assumed that the loss of the contrast enhancement fluid between the first region of interest and the second region of interest is negligible.

8. The method of claim 7 wherein it is assumed that the blood volume for the first region of interest is equal to the blood volume for the second region of interest.

9. The method of claim 2 wherein the model is a physiological model in which cardiac output and blood volume are the physiological variables, the cardiac output and the blood volume between the injection site and a measurement point of each of the regions of interest are calculated for a patient, and the at least one parameter is determined using the physiological model.

10. The method of claim 8 wherein the model is a physiological model in which cardiac output and blood volume are physiological variables, the cardiac output and the blood volume between the injection site and a measurement point of each of the regions of interest are calculated for a patient, and the at least one parameter is determined using the physiological model.

11. The method of claim 10 wherein a time to peak enhancement for first region of interest enhancement $T_1$ and a time to peak enhancement for the second region of interest enhancement $T_2$ are input into the physiological model.

12. The method of claim 11 wherein concentration at peak enhancement for the first region of interest enhancement $C_1(T_1)$ and concentration at peak enhancement for the second region of interest enhancement $C_2(T_2)$ are input into the physiological model.

13. The method of claim 12 wherein a distribution of contrast enhancement fluid in each region of interest which is injected from a peripheral injection site is described by the following physiological model analytical solution:

$$C_o(t) = \begin{cases} \dfrac{Q_{inj}}{Q_{CO}} C_i \left(1 - e^{\frac{-Q_{CO}}{V_B} t}\right) & t \le T_{inj} \\ C_o(T_{inj}) e^{\frac{-Q_{CO}}{V_B}(t - T_{inj})} & t > T_{inj} \end{cases}$$

wherein the origin, t=0, corresponds to the time at which contrast arrives in the region of interest, $Q_{inj}$[ml/s] is the injection flow rate, $T_{inj}$[s] is the injection duration, $Q_{CO}$ is the cardiac output [ml/s], $V_B$ is the blood volume [ml] between the injection site and a measurement point of each of the regions of interest, $C_i$ is the concentration of contrast in a contrast source from which contrast is injected into the patient, and $C_o(t)$ is the blood concentration in the region of interest of the agent at time t.

14. The method of claim 13 wherein concentration is related to enhancement level by the formula:

$$C_O(t) = s(t)/K$$

wherein s(t) [Hounsfield units or HU] is enhancement level at time t and K [mgI/ml] is a conversion factor.

15. The method of claim 14 wherein $T_{inj}$ is the injection duration and is amount of time between arrival of the contrast enhancement agent and the time to peak enhancement.

16. The method of claim 15 wherein:

$$C_o(T_{inj}) = \frac{\max s_2(T_2)}{K} = C_2(T_2)$$

wherein max $s_2(T_2)$ [Hu] is the maximum enhancement level in the second region of interest and $C_2(T_2)$ is the concentration at peak enhancement for the second region of interest enhancement.

17. The method of claim 14 wherein concentration in the first region of interest $C_1$ at time $T_2$ is estimated by the following formula:

$$C_1(T_2) \approx C_1(T_1) C_2(T_2)$$

wherein $C_1(T_1)$ is the concentration in the first region of interest $C_1$ at time $T_1$ and $C_2(T_2)$ is the concentration in the second region of interest $C_2$ at time $T_2$.

18. The method of claim 17 wherein blood volume $V_B$ is determined using one of the following formulas:

$$V_B = \frac{-T_1 Q_{CO}}{\log\left[1 - \dfrac{C_1(T_1)}{Q_{inj} C_i} Q_{CO}\right]} \quad V_B = \frac{-(T_2 T_1) Q_{CO}}{\log\left[\dfrac{C_1(T_1) - C_2(T_2)}{C_1(T_1)}\right]}.$$

19. The method of claim 18 wherein cardiac output $Q_{CO}$ is determined using the following formula:

$$Q_{CO} = \frac{Q_{inj}}{C(T_1)} C_i \left[1 - \left(\frac{C_1(T_1) - C_2(T_2)}{C_1(T_1)}\right)\right]^{\frac{T_1}{T_2 - T_1}}.$$

20. The method of claim 19 wherein the determined value of $Q_{CO}$ is used in the physiological model to determine the at least one parameter.

21. The of claim 20 wherein concentration of contrast agent at peak enhancement $C(T_{Peak})$ at the time of peak enhancement $T_{Peak}$ in the second region of interest of an imaging injection is related to the injection flow rate $Q_{inj}$ of the imaging injection and the injection duration $T_{inj}$ of the imaging injection using the formula:

$$C(T_{Peak}) = \frac{Q_{inj}}{Q_{CO}} C_i \left[1 - e^{-\frac{Q_{CO}}{V_B} T_{inj}}\right].$$

22. The method of claim 21 wherein a concentration of contrast agent in the second region of interest at time of a scan start, $C(T_{start})$, is provided by:

$$C(T_{start}) = \frac{\frac{Q_{inj}}{Q_{CO}} C_i \left[1 - e^{-\frac{Q_{CO}}{V_B} T_{inj}}\right]}{1 - e^{-\frac{Q_{CO}}{V_B} T_{inj}} + e^{-\frac{Q_{CO}}{V_B}(T_{inj} - \Delta T)}}$$

wherein $\Delta T$ is the scan duration and wherein $C(T_{start})$ is equal to $C(T_{start} + \Delta T)$.

23. The method of claim 22 wherein $C(T_{Peak})$ and $C(T_{start})$ enhancements are determined for admissible input values for $T_{inj}$ and $Q_{inj}$ wherein a maximum $Q_{inj}$ and a minimum $Q_{inj}$ and a maximum $T_{inj}$ and a minimum $T_{inj}$ are established.

24. The method of claim 23 wherein maximum $T_{inj}$ is established as a function of scan duration plus a constant, minimum $T_{inj}$ is established as the scan duration.

25. The method of claim 24 wherein values for a diagnostic protocol flow rate $Q^*_{inj}$ and an injection duration $T^*_{inj}$ are determined which are the arguments that minimize the cost function:

$$Q^*_{inj}, T^*_{inj} = \underset{Q_{inj}, T_{inj}}{\operatorname{argmin}} (|DesiredPeak - C(T_{Peak})| + |DesiredTarget - C(T_{start})|).$$

26. The method of claim 20 wherein the first region of interest is the pulmonary artery and the second region of interest is the ascending aorta and values for a diagnostic protocol flow rate are determined which are the arguments that minimize the cost function:

$T^*_{start}, Q^*_{inj}, R^*_1, \Delta T^*_{inj1}, R^*_2,$ $$\Delta T^*_{inj2} = \underset{\substack{T_{start}, Q_{inj}, \\ R_1, \Delta T_{inj1}, \\ R_2, \Delta T_{inj2}}}{\operatorname{argmin}} \begin{pmatrix} |C_{LH-Peak} - C_{LH-Peak-Desired}| + \\ |C_{LH-Start} - C_{LH-Target-Desired}| + \\ |C_{LH-End} - C_{LH-Target-Desired}| + \\ \alpha |C_{RH-Start} - C_{RH-Target-Desired}| + \\ \alpha |C_{RH-End} - C_{RH-Target-Desired}| + \\ \beta |Q_{inj} - Q_{TB}| + \\ \gamma, \text{if}(Q_{inj}(R_1 \Delta T_{inj1} + R_2 \Delta T_{inj2}) > V_{Load}) \end{pmatrix}$$

wherein $T_{start}$ is a time of start of a scan, $R_1$ is a rate of injection in a phase wherein only contrast medium is injected, $\Delta T_{inj1}$ is the time of duration of the phase wherein only contrast medium is injected, $R_2$ is a rate of injection in a phase wherein contrast medium and diluent are injected, $\Delta T_{inj2}$ is the time of duration of the phase wherein contrast medium and diluent are injected, $C_{LH-Peak}$ is a calculated concentration at peak enhancement in the left heart, $C_{LH-Desired}$ is a desired concentration at peak enhancement in the left heart, $C_{LH-Start}$ is a calculated concentration in the left heart at the time of start of the scan, $C_{LH-Target-Desired}$ is a desired concentration in the left heart at the time of start of the scan, $C_{LH-End}$ is a calculated concentration in the left heart at the time of the end of the scan or $T_{End}$, $C_{RH-Start}$ is a calculated concentration in the right heart at the time of start of the scan, $C_{RH-Target-Desired}$ is a desired concentration in the right heart at the time of start of the scan, and $C_{RH-End}$ is a calculated concentration in the right heart at the time of the end of the scan, $\alpha$ is a weighting factor, $\beta$ is a weighting factor and $\gamma$ is a penalty value, wherein $\gamma$ is not zero if $(Q_{inj}(R_1\Delta T_{inj1}+R_2\Delta T_{inj2})>V_{Load})$ is true and is zero if $(Q_{inj}(R_1\Delta T_{inj1}+R_2\Delta T_{inj2})>V_{load})$ is not true, wherein $V_{Load}$ is the total volume of contrast available.

27. The method of claim 26 wherein $C_{LH-Peak}$ is the greater of the value calculated as follows:

$$C_{LH-Peak} = \frac{Q_{inj}}{Q_{CO}} C_i R_1 \left(1 - e^{-\frac{Q_{CO}}{V_B} \Delta T_{inj1}}\right) \text{ or }$$

$$C_{LH-Peak} = \frac{Q_{inj}}{Q_{CO}} C_i R_1 \left(1 - e^{-\frac{Q_{CO}}{V_B} \Delta T_{inj1}}\right) e^{-\frac{Q_{CO}}{V_B} \Delta T_{inj2}} + \frac{Q_{inj}}{Q_{CO}} C_i R_2 \left(1 - e^{-\frac{Q_{CO}}{V_B} \Delta T_{inj2}}\right).$$

28. The method of claim 27 wherein concentration $C_T$ in the right heart or the left heart as applicable at a time T, which is either $T_{start}$ or $T_{end}$, when $T<(T_{arr}+\Delta T_{inj1})$, wherein $T_{arr}$ is either the time of arrival of contrast at the right heart or at the left heart as applicable, is calculated by the following formula:

$$C_T = \frac{Q_{inj}}{Q_{CO}} C_i R_1 \left(1 - e^{-\frac{Q_{CO}}{V_B}(T - T_{arr})}\right).$$

29. The method of claim 27 wherein concentration $C_T$ in the right heart or the left heart as applicable at a time T, when $(T_{arr}+\Delta T_{inj1})<T<(T_{arr}+\Delta T_{inj1}+\Delta T_{inj2})$, is calculated by the following formula:

$$C_T = \frac{Q_{inj}}{Q_{CO}} C_i R_1 \left(1 - e^{-\frac{Q_{CO}}{V_B}\Delta T_{inj1}}\right) e^{-\frac{Q_{CO}}{V_B}(T-(T_{arr}+\Delta T_{inj1}))} +$$

$$\frac{Q_{inj}}{Q_{CO}} C_i R_2 \left(1 - e^{-\frac{Q_{CO}}{V_B}(T-(T_{arr}+\Delta T_{inj1}))}\right).$$

30. The method of claim 27 wherein concentration $C_T$ in the right heart or the left heart as applicable at a time T, when, $T > (T_{arr} + \Delta T_{injA} + \Delta T_{injAB})$ is calculated by the following formula:

$$C_T = \left(\begin{array}{l} \frac{Q_{inj}}{Q_{CO}} C_i R_1 \left(1 - e^{-\frac{Q_{CO}}{V_B}\Delta T_{inj1}}\right) e^{-\frac{Q_{CO}}{V_B}\Delta T_{inj2}} + \\ \frac{Q_{inj}}{Q_{CO}} C_i R_2 \left(1 - e^{-\frac{Q_{CO}}{V_B}\Delta T_{inj2}}\right) \end{array}\right) e^{-\frac{Q_{CO}}{V_B}(T-(T_{arr}+\Delta T_{inj1}+\Delta T_{inj2}))}.$$

31. The method of claim 2 wherein the first region of interest is the pulmonary artery and the second region of interest is the ascending aorta.

32. The method of claim 2 wherein the physiological variables are used in connection with the model or at least one other model to determine the at least one parameter.

33. The method of claim 32 wherein the at least one other model is a parametric model.

34. The method of claim 1 wherein the steps (d) and (e) include:

(I) one of two equations for blood volume, $V_B$:

$$V_B = \frac{-T_1 Q_{CO}}{\log\left[1 - \frac{C_1(T_1)}{Q_{inj}C_i}Q_{CO}\right]} \quad V_B = \frac{-(T_2 - T_1)Q_{CO}}{\log\left[\frac{C_1(T_1) - C_2(T_2)}{C_1(T_1)}\right]}$$

and an equation for cardiac output, $Q_{CO}$:

$$Q_{CO} = \frac{Q_{inj}}{C(T_1)} C_i \left[1 - \left(\frac{C_1(T_1) - C_2(T_2)}{C_1(T_1)}\right)\right]^{\frac{T_1}{T_2-T_1}}$$

into which at least the pair of measurements of each of the discrete data points are input to solve for the blood volume, $V_B$, and the cardiac output, $Q_{CO}$; and (II) an automated iterative process involving use of at least the following equations:

$$C(T_{Peak}) = \frac{Q_{inj}}{Q_{CO}} C_i \left[1 - e^{-\frac{Q_{CO}}{V_B}T_{inj}}\right]$$

and $$C(T_{start}) = \frac{\frac{Q_{inj}}{Q_{CO}} C_i \left[1 - e^{-\frac{Q_{CO}}{V_B}T_{inj}}\right]}{1 - e^{-\frac{Q_{CO}}{V_B}T_{inj}} + e^{-\frac{Q_{CO}}{V_B}(T_{inj}-\Delta T)}}$$

into which the blood volume, $V_B$, and the cardiac output, $Q_{CO}$, are input and into which maximum through minimum values for each of at least an injection flow rate, $Q_{inj}$, and an injection duration, $T_{inj}$, are input iteratively to ascertain values for $C(T_{Peak})$ and $C(T_{start})$ that minimize the cost function:

$$Q_{inj}^*, T_{inj}^* = \underset{Q_{inj}, T_{inj}}{\arg\min}(|DesiredPeak - C(T_{Peak})| + |DesiredTarget - C(T_{start})|)$$

such that the values for the injection flow rate, $Q_{inj}$, and the injection duration, $T_{inj}$, that minimize the cost function are two of the at least one parameter of the injection procedure to be performed, wherein $C(T_{Peak})$ is a concentration of the contrast enhancing agent at peak enhancement and $C(T_{start})$ is a concentration of the contrast enhancing agent at a time of a start of the scanning by the imaging system, and the values of desired peak concentration, DesiredPeak, and desired target concentration, DesiredTarget, of the contrast enhancing agent in at least one of the at least two regions of interest are operator-entered into the cost function.

35. The method of claim 1 wherein the steps (d) and (e) include:

(I) one of two equations for blood volume, $V_B$:

$$V_B = \frac{-T_1 Q_{CO}}{\log\left[1 - \frac{C_1(T_1)}{Q_{inj}C_i}Q_{CO}\right]} \quad V_B = \frac{-(T_2 - T_1)Q_{CO}}{\log\left[\frac{C_1(T_1) - C_2(T_2)}{C_1(T_1)}\right]}$$

and an equation for cardiac output, $Q_{CO}$:

$$Q_{CO} = \frac{Q_{inj}}{C(T_1)} C_i \left[1 - \left(\frac{C_1(T_1) - C_2(T_2)}{C_1(T_1)}\right)\right]^{\frac{T_1}{T_2-T_1}}$$

into which at least the pair of measurements of each of the discrete data points are input to solve for the blood volume, $V_B$, and the cardiac output, $Q_{CO}$; and (II) an automated iterative process involving use of at least the following equations:

$$C(T_{Peak}) = \frac{Q_{inj}}{Q_{CO}} C_i \left[1 - e^{-\frac{Q_{CO}}{V_B}T_{inj}}\right]$$

and $$C(T_{start}) = \frac{\frac{Q_{inj}}{Q_{CO}} C_i \left[1 - e^{-\frac{Q_{CO}}{V_B}T_{inj}}\right]}{1 - e^{-\frac{Q_{CO}}{V_B}T_{inj}} + e^{-\frac{Q_{CO}}{V_B}(T_{inj}-\Delta T)}}$$

into which the blood volume, $V_B$, and the cardiac output, $Q_{CO}$, are input and into which maximum through minimum values for each of at least an injection flow rate, $Q_{inj}$, and an injection duration, $T_{inj}$, are input iteratively to ascertain values for $C(T_{Peak})$ and $C(T_{start})$ that minimize the cost function:

$T^*_{start}, Q^*_{inj}, R^*_1, \Delta T^*_{inj1}, R^*_2,$ $$\Delta T^*_{inj2} = \underset{\substack{T_{start}, Q_{inj}, \\ R_1, \Delta T_{inj1}, \\ R_2, \Delta T_{inj2}}}{\arg\min} \begin{pmatrix} |C_{LH-Peak} - C_{LH-Peak-Desired}| + \\ |C_{LH-Start} - C_{LH-Target-Desired}| + \\ |C_{LH-End} - C_{LH-Target-Desired}| + \\ \alpha|C_{RH-Start} - C_{RH-Target-Desired}| + \\ \alpha|C_{RH-End} - C_{RH-Target-Desired}| + \\ \beta|Q_{inj} - Q_{TB}| + \\ \gamma, \text{ if } (Q_{inj}(R_1 \Delta T_{inj1} + R_2 \Delta T_{inj2}) > V_{Load}) \end{pmatrix}$$

such that the values for the injection flow rate, $Q_{inj}$, and the injection duration, $T_{inj}$, that minimize the cost function are two of the at least one parameter of the procedure to be performed, wherein $C(T_{Peak})$ is a concentration of the contrast enhancing agent at peak enhancement and $C(T_{start})$ is a concentration of the contrast enhancing agent at a time of a start of the scanning by the imaging system, and wherein $T_{start}$ is a time of start of a scan, $R_1$ is a rate of injection in a phase wherein only contrast medium is injected, $\Delta T_{inj1}$ is the time of duration of the phase wherein only contrast medium is injected, $R_2$ is a rate of injection in a phase wherein contrast medium and diluent are injected, $\Delta T_{inj2}$ is the time of duration of the phase wherein contrast medium and diluent are injected, $C_{LH-Peak}$ is a calculated concentration at peak enhancement in the left heart, $C_{LH-Desired}$ is a desired concentration at peak enhancement in the left heart, $C_{LH-Start}$ is a calculated concentration in the left heart at the time of start of the scan, $C_{LH-Target-Desired}$ is a desired concentration in the left heart at the time of start of the scan, $C_{LH-End}$ is a calculated concentration in the left heart at the time of the end of the scan or $T_{End}$, $C_{RH-Start}$ is a calculated concentration in the right heart at the time of start of the scan, $C_{RH-Target-Desired}$ is a desired concentration in the right heart at the time of start of the scan, and $C_{RH-End}$ is a calculated concentration in the right heart at the time of the end of the scan, α is a weighting factor, β is a weighting factor and γ is a penalty value, wherein γ is not zero if $(Q_{inj}(R_1 \Delta T_{inj1} + R_2 \Delta T_{inj2}) > V_{Load})$ is true and is zero if $(Q_{inj}(R_1 \Delta T_{inj1} + R_2 \Delta T_{inj2}) > V_{Load})$ is not true, wherein $V_{Load}$ is the total volume of contrast available, and the values of desired peak concentration, DesiredPeak, and desired target concentration, DesiredTarget, of the contrast enhancing agent in at least one of the at least two regions of interest are operator-entered into the cost function.

36. A method of determining at least one parameter for a procedure, the method comprising the steps of:
(a) injecting a test bolus of a pharmaceutical;
(b) measuring at least two regions of interest with a sensor as the test bolus of the pharmaceutical flows therethrough to obtain therefrom a time concentration curve for each of the at least two regions of interest;
(c) extracting at least one discrete data point from each of the time concentration curves such that each of the discrete data points constitutes a pair of measurements on the time concentration curve corresponding thereto; and
(d) determining the at least one parameter for the procedure to be performed by substituting into a model the discrete data points extracted from the time concentration curves.

37. The method of claim 36 wherein a sufficient number of the discrete data points are substituted into the model to determine values for physiological variables in the model, the variables being related to cardiopulmonary function and for use in determining the at least one parameter for the procedure to be performed.

38. The method of claim 36 wherein the step of substituting the discrete data points into the model for use in determining the at least one parameter for the procedure includes:
(a) one of two equations for blood volume, $V_B$:

$$V_B = \frac{-T_1 Q_{CO}}{\log\left[1 - \frac{C_1(T_1)}{Q_{inj}C_i}Q_{CO}\right]} \quad V_B = \frac{-(T_2 - T_1)Q_{CO}}{\log\left[\frac{C_1(T_1) - C_2(T_2)}{C_1(T_1)}\right]}$$

and an equation for cardiac output, $Q_{CO}$:

$$Q_{CO} = \frac{Q_{inj}}{C(T_1)} C_i \left[1 - \left(\frac{C_1(T_1) - C_2(T_2)}{C_1(T_1)}\right)\right]^{\frac{T_1}{T_2 - T_1}}$$

into which at least the pair of measurements of each of the discrete data points are input to solve for the blood volume, $V_B$, and the cardiac output, $Q_{CO}$; and
(b) an automated iterative process involving use of at least the following equations:

$$C(T_{Peak}) = \frac{Q_{inj}}{Q_{CO}} C_i \left[1 - e^{\frac{-Q_{CO}}{V_B} T_{inj}}\right]$$

and $$C(T_{start}) = \frac{\frac{Q_{inj}}{Q_{CO}} C_i \left[1 - e^{\frac{-Q_{CO}}{V_B} T_{inj}}\right]}{1 - e^{\frac{-Q_{CO}}{V_B} T_{inj}} + e^{\frac{-Q_{CO}}{V_B}(T_{inj} - \Delta T)}}$$

into which the blood volume, $V_B$, and the cardiac output, $Q_{CO}$, are input and into which maximum through minimum values for each of at least an injection flow rate, $Q_{inj}$, and an injection duration, $T_{inj}$, are input iteratively to ascertain values for $C(T_{Peak})$ and $C(T_{start})$ that minimize the cost function:

$$Q^*_{inj}, T^*_{inj} = \underset{Q_{inj}, T_{inj}}{\arg\min}(|DesiredPeak - C(T_{Peak})| + |DesiredTarget - C(T_{start})|)$$

such that the values for the injection flow rate, $Q_{inj}$, and the injection duration, $T_{inj}$, that minimize the cost function are two of the at least one parameter of the procedure, wherein $C(T_{Peak})$ is a concentration of the pharmaceutical at peak enhancement and $C(T_{start})$ is a concentration of the pharmaceutical at a time of a start of the measurement by the sensor, and the values of desired peak concentration, DesiredPeak, and desired target concentration, DesiredTarget, of the pharmaceutical in at least one of the at least two regions of interest are operator-entered into the cost function.

39. The method of claim 36 wherein the step of substituting the discrete data points into the model for use in determining the at least one parameter for the procedure includes:

(a) one of two equations for blood volume, $V_B$:

$$V_B = \frac{-T_1 Q_{CO}}{\log\left[1 - \frac{C_1(T_1)}{Q_{inj}C_i}Q_{CO}\right]} \quad V_B = \frac{-(T_2 - T_1)Q_{CO}}{\log\left[\frac{C_1(T_1) - C_2(T_2)}{C_1(T_1)}\right]}$$

and an equation for cardiac output, $Q_{CO}$:

$$Q_{CO} = \frac{Q_{inj}}{C(T_1)} C_i \left[1 - \left(\frac{C_1(T_1) - C_2(T_2)}{C_1(T_1)}\right)\right]^{\frac{T_1}{T_2 - T_1}}$$

into which at least the pair of measurements of each of the discrete data points are input to solve for the blood volume, $V_B$, and the cardiac output, $Q_{CO}$; and (b) an automated iterative process involving use of at least the following equations:

$$C(T_{Peak}) = \frac{Q_{inj}}{Q_{CO}} C_i \left[1 - e^{\frac{-Q_{CO}}{V_B} T_{inj}}\right]$$

and $$C(T_{start}) = \frac{\frac{Q_{inj}}{Q_{CO}} C_i \left[1 - e^{\frac{-Q_{CO}}{V_B} T_{inj}}\right]}{1 - e^{\frac{-Q_{CO}}{V_B} T_{inj}} + e^{\frac{-Q_{CO}}{V_B}(T_{inj} - \Delta T)}}$$

into which the blood volume, $V_B$, and the cardiac output, $Q_{CO}$, are input and into which maximum through minimum values for each of at least an injection flow rate, $Q_{inj}$, and an injection duration, $T_{inj}$, are input iteratively to ascertain values for $C(T_{Peak})$ and $C(T_{start})$ that minimize the cost function:

$T^*_{start}, Q^*_{inj}, R^*_1, \Delta T^*_{inj1}, R^*_2,$ $$\Delta T^*_{inj2} = \arg\min_{\substack{T_{start}, Q_{inj}, \\ R_1, \Delta T_{inj1}, \\ R_2, \Delta T_{inj2}}} \begin{pmatrix} |C_{LH-Peak} - C_{LH-Peak-Desired}| + \\ |C_{LH-Start} - C_{LH-Target-Desired}| + \\ |C_{LH-End} - C_{LH-Target-Desired}| + \\ \alpha|C_{RH-Start} - C_{RH-Target-Desired}| + \\ \alpha|C_{RH-End} - C_{RH-Target-Desired}| + \\ \beta|Q_{inj} - Q_{TB}| + \\ \gamma, \text{ if } (Q_{inj}(R_1\Delta T_{inj1} + R_2\Delta T_{inj2}) > V_{Load}) \end{pmatrix}$$

such that the values for the injection flow rate, $Q_{inj}$, and the injection duration, $T_{inj}$, that minimize the cost function are two of the at least one parameter of the procedure, wherein $C(T_{Peak})$ is a concentration of the pharmaceutical at peak enhancement and $C(T_{start})$ is a concentration of the pharmaceutical at a time of a start of the measurement by the sensor, and wherein $T_{start}$ is a time of start of the measurement, $R_1$ is a rate of injection in a phase wherein only the pharmaceutical is injected, $\Delta T_{inj1}$ is the time of duration of the phase wherein only the pharmaceutical is injected, $R_2$ is a rate of injection in a phase wherein the pharmaceutical and diluent are injected, $\Delta T_{inj2}$ is the time of duration of the phase wherein the pharmaceutical and diluent are injected, $C_{LH-Peak}$ is a calculated concentration at peak enhancement in the left heart, $C_{LH-Desired}$ is a desired concentration at peak enhancement in the left heart, $C_{LH-Start}$ is a calculated concentration in the left heart at the time of start of the measurement, $C_{LH-Target-Desired}$ is a desired concentration in the left heart at the time of start of the measurement, $C_{LH-End}$ is a calculated concentration in the left heart at the time of the end of the measurement or $T_{End}$, $C_{RH-Start}$ is a calculated concentration in the right heart at the time of start of the measurement, $C_{RH-Target-Desired}$ is a desired concentration in the right heart at the time of start of the measurement, and $C_{RH-End}$ is a calculated concentration in the right heart at the time of the end of the measurement, $\alpha$ is a weighting factor, $\beta$ is a weighting factor and $\gamma$ is a penalty value, wherein $\gamma$ is not zero if $(Q_{inj}(R_1\Delta T_{inj1}+R_2\Delta T_{inj2}) > V_{Load})$ is true and is zero if $(Q_{inj}(R_1\Delta T_{inj1}+R_2\Delta T_{inj2}) > V_{Load})$ is not true, wherein $V_{Load}$ is the total volume of the pharmaceutical available, and the values of desired peak concentration, DesiredPeak, and desired target concentration, DesiredTarget, of the pharmaceutical in at least one of the at least two regions of interest are operator-entered into the cost function.

\* \* \* \* \*

UNITED STATES PATENT AND TRADEMARK OFFICE
CERTIFICATE OF CORRECTION

PATENT NO. : 8,428,694 B2  
APPLICATION NO. : 12/669292  
DATED : April 23, 2013  
INVENTOR(S) : Kalafut et al.

Page 1 of 1

It is certified that error appears in the above-identified patent and that said Letters Patent is hereby corrected as shown below:

IN THE DRAWINGS:

In Fig. 10D, Sheet 10 of 38, delete "(Control Group)fig." and insert -- (Contol Group) --, therefor.

IN THE SPECIFICATION:

In Column 22, Line 50, delete "1 the aorta" and insert -- the aorta --, therefor.
In Column 22, Line 61, delete "Equation 8:" and insert -- Equation 8. --, therefor.

IN THE CLAIMS:

In Column 29, Line 14, in Claim 21, delete "The of" and insert -- The method of --, therefor.

Signed and Sealed this
Eighth Day of October, 2013

Teresa Stanek Rea
*Deputy Director of the United States Patent and Trademark Office*